(12) United States Patent
Ino et al.

(10) Patent No.: US 10,228,647 B2
(45) Date of Patent: *Mar. 12, 2019

(54) OPTICAL SENSOR AND IMAGE FORMING APPARATUS

(71) Applicant: CANON KABUSHIKI KAISHA, Tokyo (JP)

(72) Inventors: Kazushi Ino, Suntou-gun (JP); Takuya Mukaibara, Susono (JP); Naoki Nishimura, Susono (JP); Takashi Fukuhara, Higashikurume (JP); Osamu Nagasaki, Suntou-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/897,356

(22) Filed: Feb. 15, 2018

(65) Prior Publication Data

US 2018/0173144 A1 Jun. 21, 2018

Related U.S. Application Data

(63) Continuation of application No. 15/297,381, filed on Oct. 19, 2016, now Pat. No. 9,927,752.

(30) Foreign Application Priority Data

Nov. 6, 2015 (JP) .................................. 2015-218797

(51) Int. Cl.
    *G03G 15/00* (2006.01)
    *G03G 15/01* (2006.01)
    *G01N 21/55* (2014.01)

(52) U.S. Cl.
    CPC ..... *G03G 15/5054* (2013.01); *G03G 15/0178* (2013.01); *G03G 15/5058* (2013.01);
    (Continued)

(58) Field of Classification Search
    CPC .............................................. G01N 2021/556
    See application file for complete search history.

(56) References Cited

U.S. PATENT DOCUMENTS

9,049,313 B2 6/2015 Mukaibara et al.
9,213,290 B2 12/2015 Koyama et al.
(Continued)

FOREIGN PATENT DOCUMENTS

JP 10-221902 A 8/1998
JP 2002-014507 A 1/2002
(Continued)

OTHER PUBLICATIONS

Office Action dated Jan. 13, 2017 in Japanese Patent Application No. 2015-218797.
(Continued)

*Primary Examiner* — Clayton E Laballe
*Assistant Examiner* — Jas Sanghera
(74) *Attorney, Agent, or Firm* — Venable LLP

(57) ABSTRACT

A toner detection unit is configured by an LED that irradiates light toward an intermediate transfer belt, first and second light receiving elements that respectively receive specular reflection light and diffused reflection light of light irradiated toward the intermediate transfer belt from the LED, a circuit board, and a housing. The LED and the light receiving elements are mounted in a line on the circuit board. The housing is configured to guide, to the first light receiving element, the specular reflection light from a first region within an irradiation region on which light is irradiated from the LED on the intermediate transfer belt, and to guide, to the second light receiving element, the diffused reflection light from a second region which is different from the first region within the irradiation region.

21 Claims, 15 Drawing Sheets

(52) U.S. Cl.
CPC ............... *G01N 2021/556* (2013.01); *G03G 2215/00143* (2013.01); *G03G 2215/00616* (2013.01)

(56) References Cited

U.S. PATENT DOCUMENTS

| | | | |
|---|---|---|---|
| 9,244,415 B2 | 1/2016 | Yamaguchi et al. | |
| 9,429,513 B2 | 8/2016 | Adachi et al. | |
| 9,927,752 B2* | 3/2018 | Ino | G03G 15/5054 |
| 2004/0208661 A1 | 10/2004 | Kitagawa et al. | |
| 2004/0251435 A1 | 12/2004 | Sawayama et al. | |
| 2005/0211902 A1 | 9/2005 | Barry et al. | |
| 2011/0076040 A1 | 3/2011 | Uchidate et al. | |
| 2011/0222892 A1 | 9/2011 | Hashiguchi et al. | |
| 2013/0259510 A1 | 10/2013 | Regelsberger et al. | |
| 2013/0272740 A1 | 10/2013 | Nakagawa et al. | |
| 2015/0278662 A1 | 10/2015 | Hosoya et al. | |
| 2015/0293488 A1 | 10/2015 | Mukaibara et al. | |
| 2017/0131657 A1 | 5/2017 | Monden et al. | |
| 2017/0134604 A1 | 5/2017 | Mukaibara et al. | |

FOREIGN PATENT DOCUMENTS

| | | |
|---|---|---|
| JP | 2006-208266 A | 8/2006 |
| JP | 2010-181664 A | 8/2010 |
| JP | 2010-217532 A | 9/2010 |
| JP | 2011-107307 A | 6/2011 |
| JP | 2011-180527 A | 9/2011 |
| JP | 2013-191835 A | 9/2013 |
| JP | 2014-026225 A | 2/2014 |
| JP | 2014-095924 A | 5/2014 |
| JP | 2015-108611 A | 6/2015 |
| WO | 2013/121767 A1 | 8/2013 |

OTHER PUBLICATIONS

Extended European Search Report dated Mar. 22, 2017, in European Patent Application No. 16193455.9.

* cited by examiner

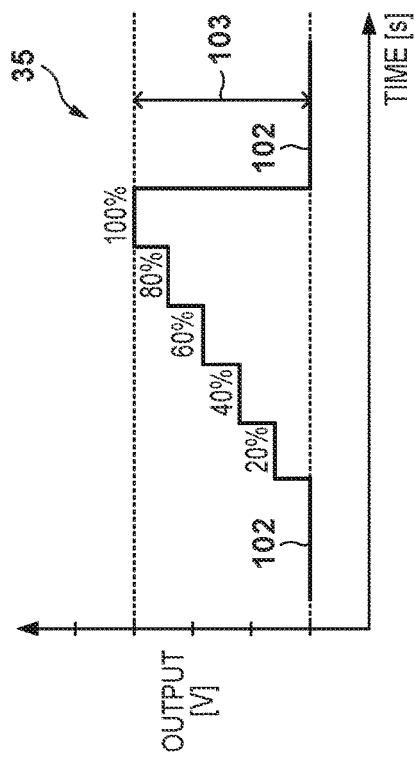
FIG. 10A
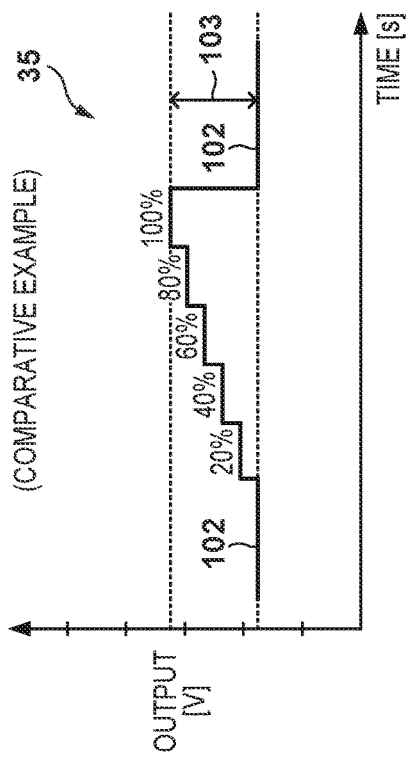
FIG. 10B
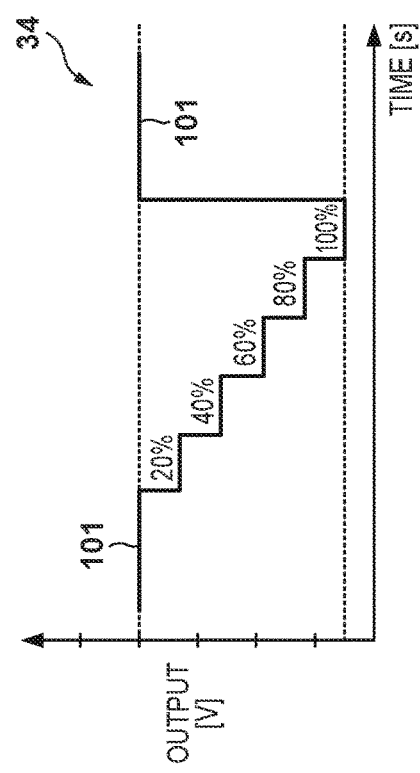
FIG. 10C (COMPARATIVE EXAMPLE)
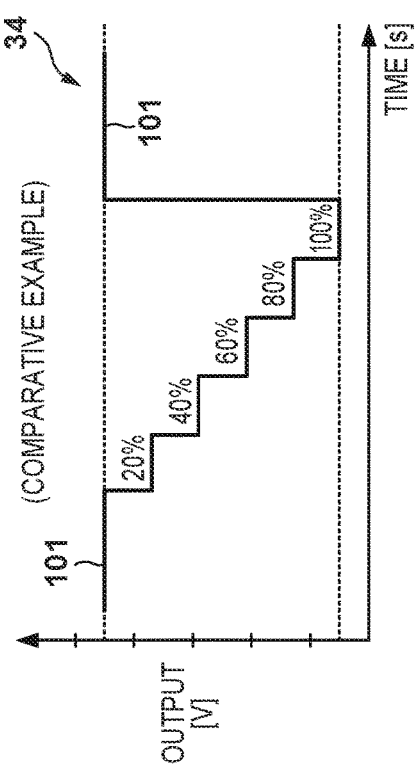
FIG. 10D (COMPARATIVE EXAMPLE)

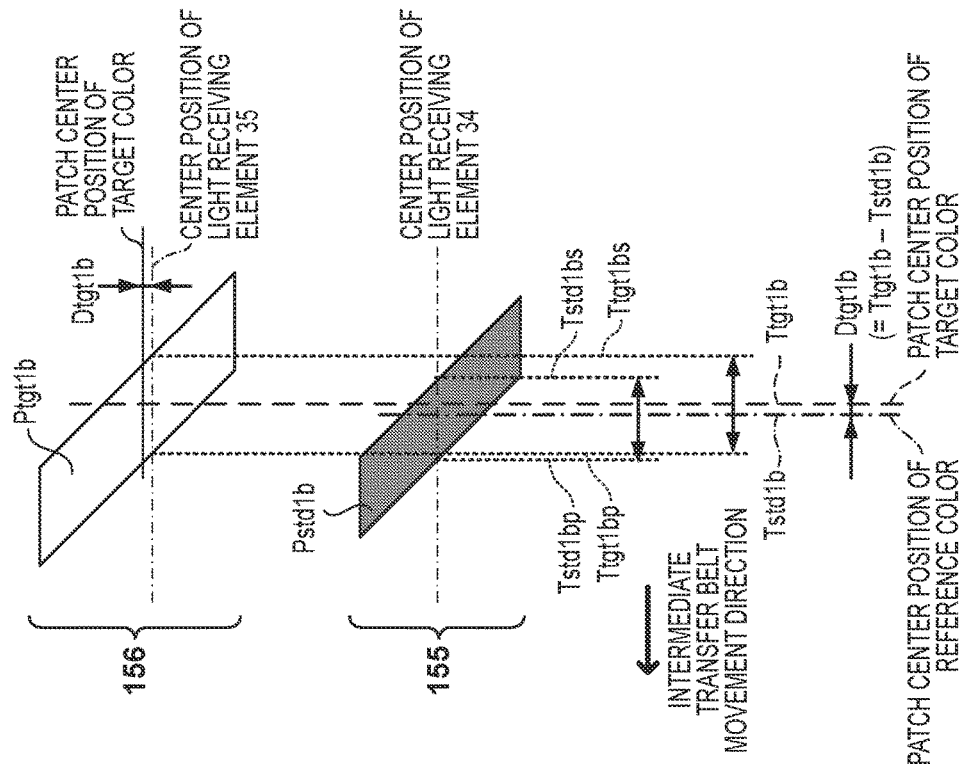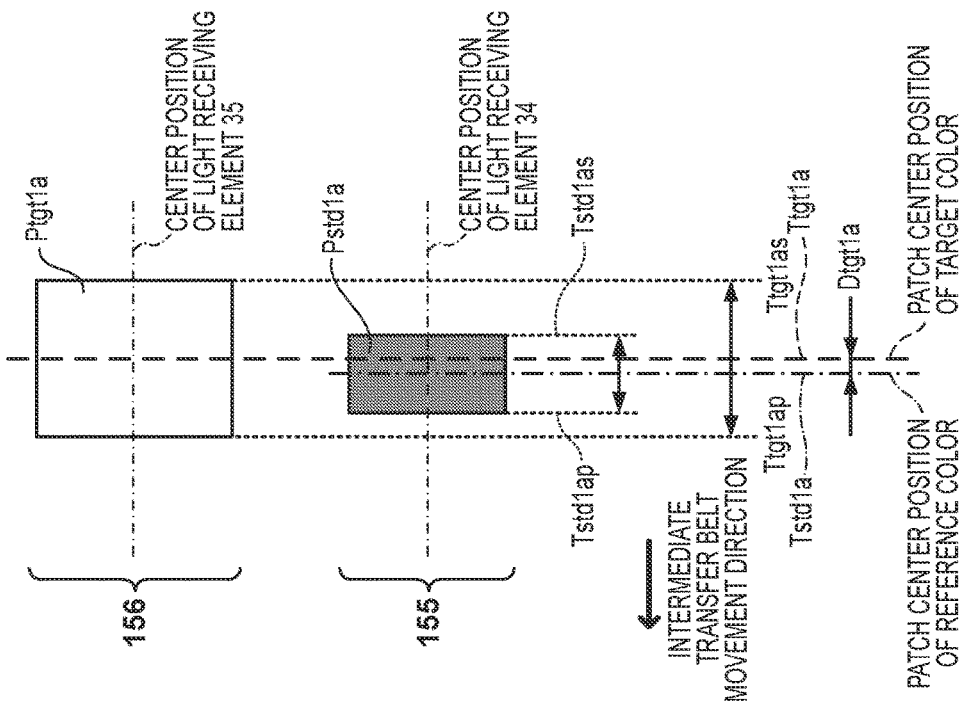
FIG. 12A
FIG. 12B

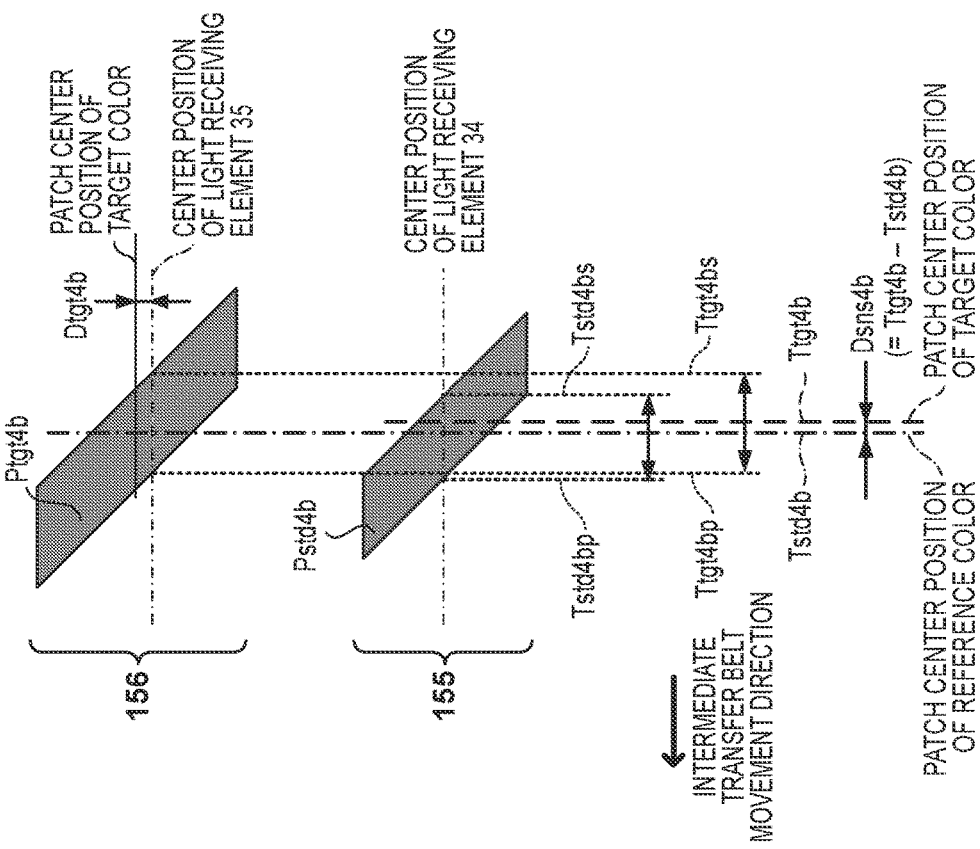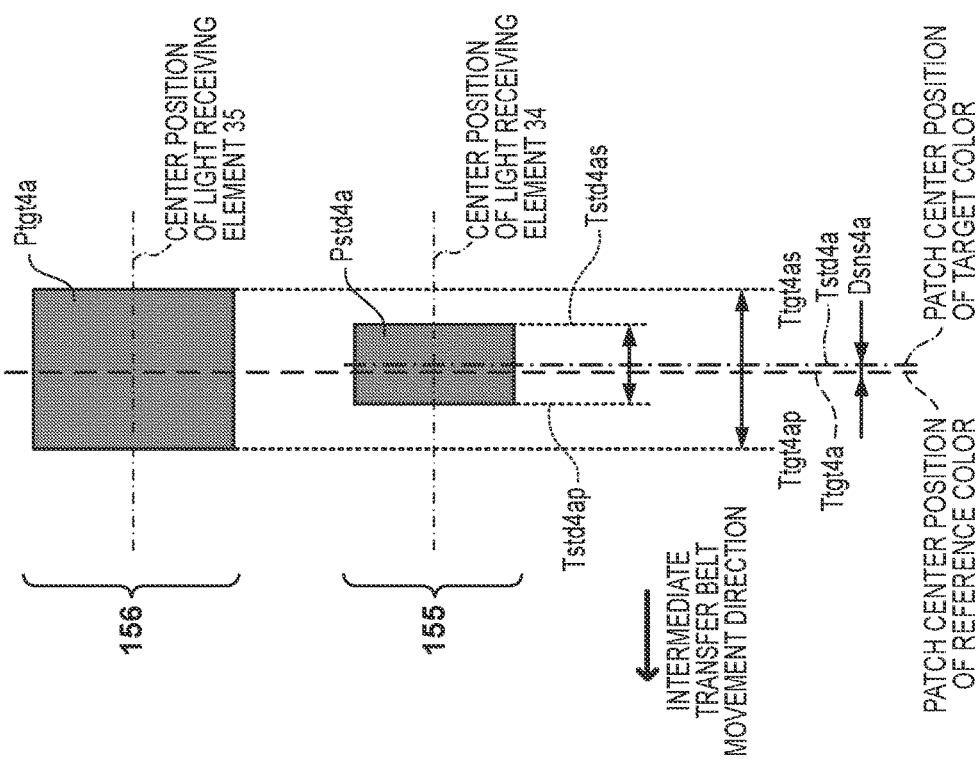

OPTICAL SENSOR AND IMAGE FORMING APPARATUS

BACKGROUND OF THE INVENTION

Field of the Invention

The present invention relates to an optical sensor for receiving, by a plurality of light receiving elements, a specular reflection light and a diffused reflection light of light emitted from a light emitting element to detect a detection target, and an image forming apparatus comprising the optical sensor.

Description of the Related Art

In recent years, in electrophotographic image forming apparatuses, a tandem type which is a configuration in which a photosensitive member is arranged for each color to accelerate printing speed has become mainstream. In a tandem type image forming apparatus, a color misregistration amount is determined by forming a detection image (a toner image) which is a test pattern for detecting a color misregistration amount on an intermediate transfer belt, for example, and then irradiating light onto the detection image and detecting light reflected therefrom by an optical sensor. Also, a determination of a density of a toner (a density of an image) using such an optical sensor has been performed. In Japanese Patent Laid-Open No. H10-221902, a technique is disclosed in which a diffused reflection light and a specular reflection light of light irradiated on a toner image are respectively received by individual light receiving units (sensors), and based on the received light amounts, the density of toner is detected. By virtue of such a technique, it is possible to improve precision of detection of toner by an optical sensor even if toner of a plurality of colors used in the image forming apparatus has reflection characteristics that differ with respect to the light used by the optical sensor.

In an optical sensor of the foregoing type, generally, in addition to providing an aperture for limiting (narrowing) light that the light emitting element emits, that kind of aperture is also provided for the light receiving elements that respectively receive specular reflection light and diffused reflection light in order to separate the specular reflection light and the diffused reflection light. Surface-mounted type optical sensors in which an optical element is mounted directly on a surface of a circuit board are disclosed as such kind of optical sensors in Japanese Patent Laid-Open No. 2006-208266 and in Japanese Patent Laid-Open No. 2013-191835.

In Japanese Patent Laid-Open No. 2006-208266, an optical unit holder is attached to a circuit board on which a light emitting element and two light receiving elements are directly mounted, and three polarization filters respectively corresponding to the light emitting element and the two light receiving elements are arranged on an outside surface of the optical unit holder. However, when a plurality of polarization filters are used in this way, it leads to an increase in apparatus cost, and a reduction in productivity. Meanwhile, in Japanese Patent Laid-Open No. 2013-191835, a housing having an opening (a light guiding path) that functions as an aperture corresponding to each optical element (the light emitting element and the two light receiving elements) is configured such that light shielding walls that configure the openings are inserted in a slit hole arranged in a circuit board. This improves a light-shielding property in an optical sensor configured by mounting each optical element on a surface of the circuit board.

However, in the optical sensor described in Japanese Patent Laid-Open No. 2013-191835, it is necessary to arrange the light emitting element and the two light receiving elements at a certain distance from each other in order to realize the housing that improves the light-shielding property. Even if it is possible to improve the light-shielding property by virtue of this kind of optical sensor configuration, the size of the optical sensor is larger in a direction in which the light emitting element and the two light receiving elements are arranged. Accordingly, it would be desirable to realize further miniaturization in the optical sensor.

SUMMARY OF THE INVENTION

The present invention was conceived in view of the above described issues. The present invention provides a technique that enables the miniaturization of an optical sensor for detecting a detection target by receiving, by different light receiving elements, a specular reflection light and a diffused reflection light of light emitted from a light emitting element.

According to one aspect of the present invention, there is provided an optical sensor, comprising: a light emitting element that irradiates an irradiating light toward an irradiated member; a first light receiving element for receiving a diffused reflection light into which the irradiating light is diffusely reflected by the irradiated member; a second light receiving element for receiving a specular reflection light into which the irradiating light is specularly reflected by the irradiated member; and a housing for forming a first opening and a second opening, wherein the first opening is an opening for determining an irradiation region of the irradiated member onto which the irradiating light is irradiated, and is the opening through which the irradiating light passes and through which the diffused reflection light to be received by the first light receiving element passes, and the second opening is an opening through which the specular reflection light received to be by the second light receiving element passes.

According to another aspect of the present invention, there is provided an optical sensor, comprising: a light emitting element that irradiates an irradiating light toward an irradiated member; a first light receiving element for receiving a diffused reflection light into which the irradiating light is diffusely reflected in an irradiation region of the irradiated member; and a second light receiving element for receiving a specular reflection light into which the irradiating light is specularly reflected in the irradiation region of the irradiated member, wherein the first light receiving element receives the diffused reflection light diffusely reflected in a first region within the irradiation region, and the second light receiving element receives the specular reflection light specularly reflected in a second region within the irradiation region, at least a part of which does not include the first region in a main scanning direction.

According to still another aspect of the present invention, there is provided an optical sensor, comprising: a light emitting element that irradiates an irradiating light toward an irradiated member; a first light receiving element for receiving a diffused reflection light into which the irradiating light is diffusely reflected in an irradiation region of the irradiated member; and a second light receiving element for receiving a specular reflection light into which the irradiating light is specularly reflected in the irradiation region of the irradiated member; and a housing for forming a first opening for guiding light emitted from the light emitting element toward the irradiated member, a second opening for guiding, to the first light receiving element, the diffused reflection light diffusely reflected in a first region within the irradiation region, and a third opening for guiding, to the second light receiving element, the specular reflection light specularly reflected in a second region within the irradiation region, at least a part of which does not include the first region in a main scanning direction.

According to yet another aspect of the present invention, there is provided an optical sensor, comprising: a light emitting element that irradiates an irradiating light toward an irradiated member; a first light receiving element for receiving a diffused reflection light into which the irradiating light is diffusely reflected by the irradiated member; a second light receiving element for receiving a specular reflection light into which the irradiating light is specularly reflected by the irradiated member; a circuit board on which the first light receiving element and the second light receiving element are arranged beside each other, wherein the first light receiving element and the second light receiving element are mounted on the circuit board as a single integrated circuit.

By virtue of the present invention, it becomes possible to miniaturize an optical sensor for detecting a detection target by receiving, by different light receiving elements, a specular reflection light and a diffused reflection light of light emitted from a light emitting element.

Further features of the present invention will become apparent from the following description of exemplary embodiments (with reference to the attached drawings).

BRIEF DESCRIPTION OF THE DRAWINGS

FIG. 10A to FIG. 10D illustrate examples of output from the two light receiving elements of the toner detection unit.

FIG. 12A and FIG. 12B illustrate examples of test patterns formed on an intermediate transfer belt (second embodiment).

FIG. 13A and FIG. 13B illustrates examples of test patterns formed on an intermediate transfer belt (third embodiment).

DESCRIPTION OF THE EMBODIMENTS

Hereinafter, embodiments of the present invention will be described in detail with reference to the accompanying drawings. It should be noted that the following embodiments are not intended to limit the scope of the appended claims, and that not all the combinations of features described in the embodiments are necessarily essential to the solving means of the present invention.

First Embodiment

Figure 1:
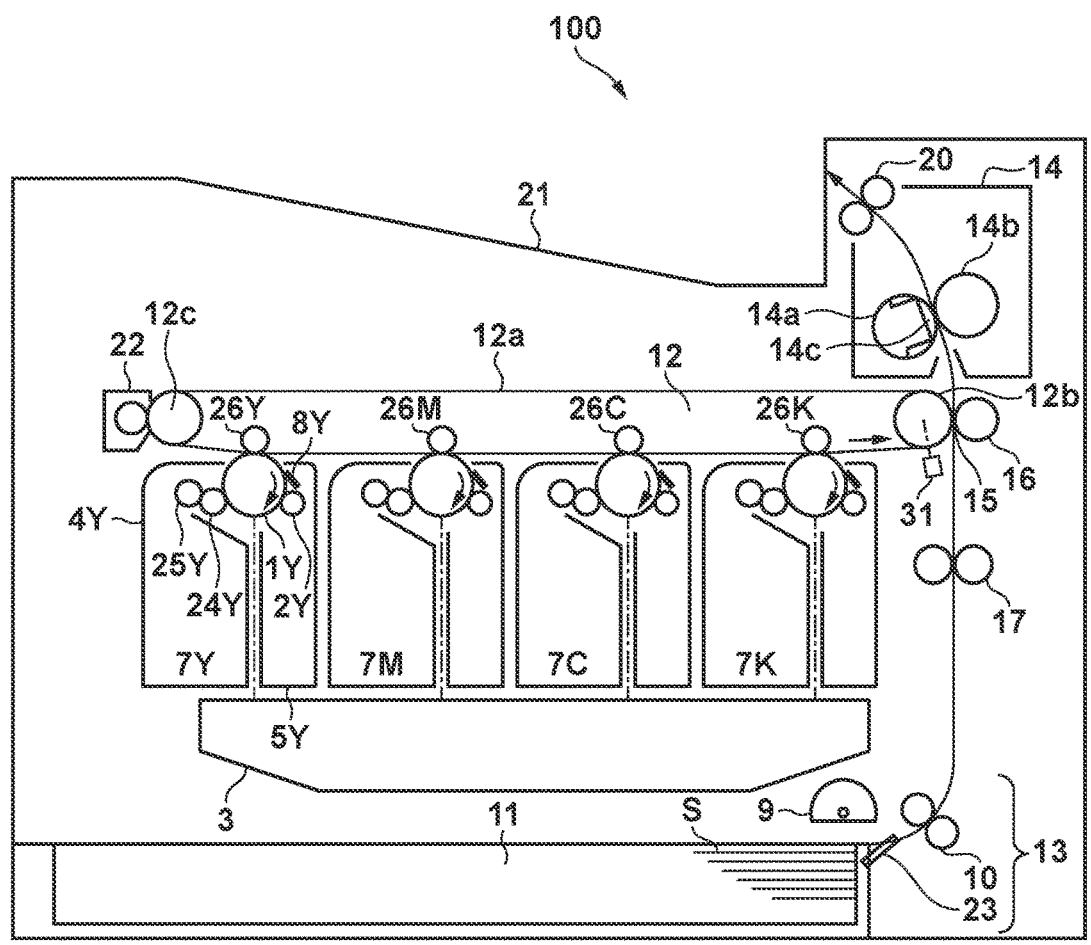
FIG. 1 is a cross-section view for illustrating an example of a hardware configuration of an image forming apparatus.

<Overview of Image Forming Apparatus>
FIG. 1 is a cross-section view for illustrating an example of a hardware configuration of an image forming apparatus 100 according to a first embodiment. The image forming apparatus 100 in the present embodiment is a color laser printer for forming a multicolor image using developing material (toner) of yellow (Y), magenta (M), cyan (C), and black (K). The image forming apparatus 100 may also be any of the following: for example a print apparatus, a printer, a copying machine, a multi function peripheral (MFP), or a facsimile apparatus. Note that Y, M, C, or K on the end of reference numerals indicates that the color of the developing material (toner) of the corresponding component is yellow, magenta, cyan, or black. In the following explanation, reference numerals are used omitting the Y, M, C, or K on the end in a case where it is not necessary to distinguish the color.

The image forming apparatus 100 is equipped with 4 process cartridges 7 (process cartridges 7Y, 7M, 7C, and 7K) corresponding to image forming stations for forming images of Y, M, C, and K respectively. In FIG. 1, reference numerals are given only for components of the process cartridge 7Y corresponding to Y, but the same configuration is employed for the four process cartridges 7Y, 7M, 7C, and 7K. However, the four process cartridges 7Y, 7M, 7C, and 7K are different in that they form images by respectively different colored (Y, M, C, and K) toner.

In a periphery of a photosensitive drum 1, a charging roller 2, an exposure unit 3, a developing unit 4, a primary transfer roller 26, and a cleaning blade 8 are arranged sequentially in a rotation direction. In the present embodiment, the photosensitive drum 1, the charging roller 2, the developing unit 4 and the cleaning blade 8 are integrated into the process cartridge 7 which can be attached/removed to/from the image forming apparatus 100. The exposure unit 3 is arranged on a lower side in a vertical direction of the process cartridge 7.

The process cartridge 7 is configured by the developing unit 4 and a cleaner unit 5. The developing unit 4 includes a developing roller 24, a developing material coating roller 25, and a toner container. Toner of the corresponding color is contained in a toner container. The developing roller 24 is rotated by a drive motor (not shown), a developing bias voltage is applied from a high voltage power supply 44 (FIG. 2), and development of an electrostatic latent image is performed using toner contained in the toner container. The cleaner unit 5 includes the photosensitive drum 1, the charging roller 2, the cleaning blade 8, and a waste toner container.

The photosensitive drum 1 is configured by an organic photo conductor layer (OPC) coated on an outer surface of an aluminum cylinder. The photosensitive drum 1 is supported to be rotatable by flanges on both ends, and is rotated in a direction of an arrow illustrated in FIG. 1 by a driving force being transferred from a drive motor (not shown) to one end. The charging roller 2 uniformly charges the surface of the photosensitive drum 1 to a predetermined electric potential. The exposure unit 3 irradiates a laser beam on the photosensitive drum 1 to expose the photosensitive drum 1 based on image information (image signal), thereby forming an electrostatic latent image on the photosensitive drum 1. The developing unit 4 forms a toner image on the photosensitive drum 1 by causing toner to attach in an electrostatic latent image on the photosensitive drum 1 and then developing the electrostatic latent image.

Figure 2:
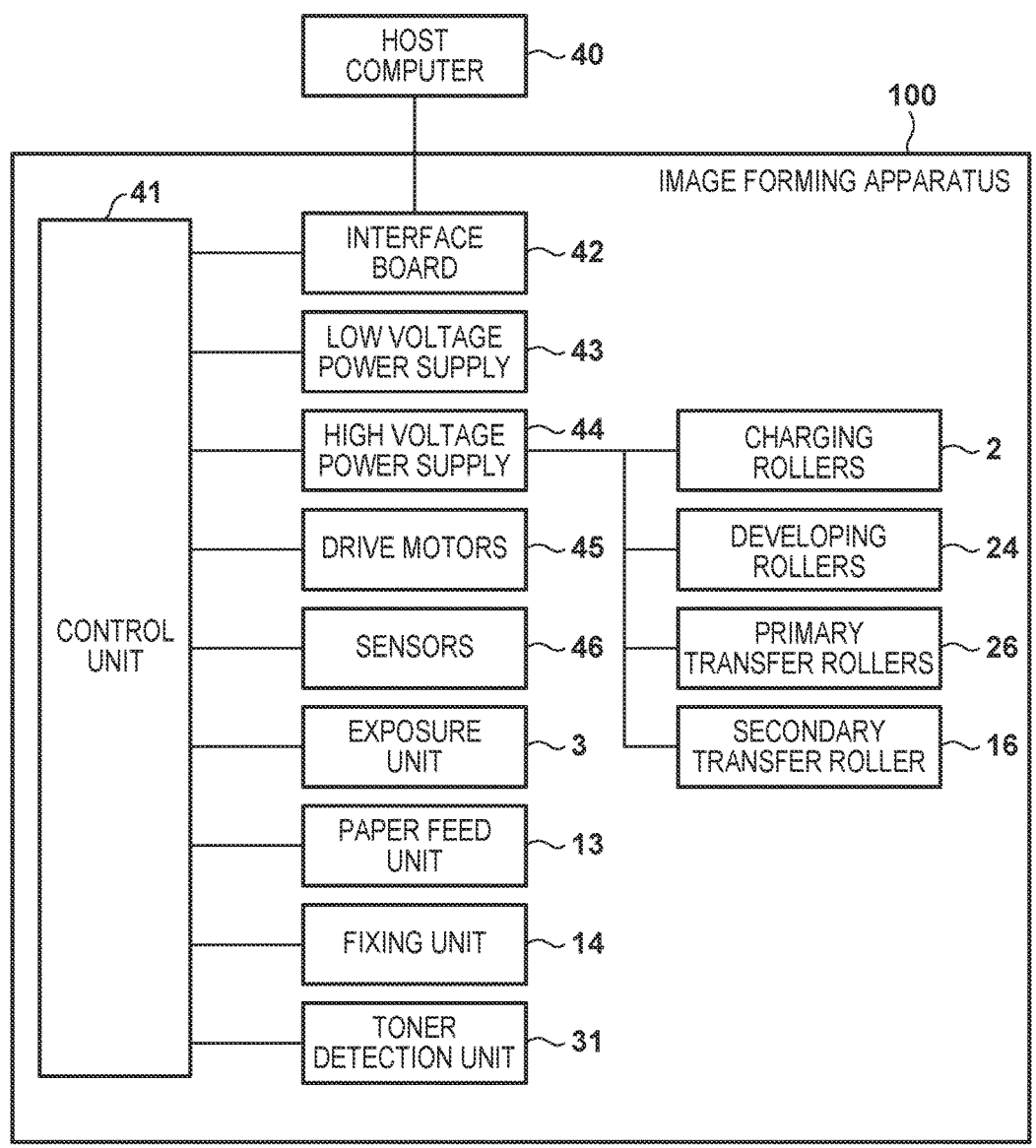
FIG. 2 is a block diagram illustrating an example configuration of a control system of the image forming apparatus.

An intermediate transfer belt 12a, a driving roller 12b, and a tension roller 12c configure an intermediate transfer unit 12. The intermediate transfer belt 12a is stretched between the driving roller 12b and the tension roller 12c, and moves (rotates) in a direction of an arrow illustrated in FIG. 1 by a rotation of the driving roller 12b. In the present embodiment, the intermediate transfer belt 12a is an example of an image carrier which is rotated. At a position inside of the intermediate transfer belt 12a and facing the photosensitive drum 1, the primary transfer roller 26 is arranged. The primary transfer roller 26 transfers a toner image on the photosensitive drum 1 onto the intermediate transfer belt 12a (an intermediate transfer member) by a transfer bias voltage applied from the high voltage power supply 44 (FIG. 2). Toner images of the four colors respectively formed on the photosensitive drums 1Y, 1M, 1C, and 1K are transferred (primary transfer) on the intermediate transfer belt 12a sequentially so as to overlap each other. Thus, a multicolor toner image composed of Y, M, C, and K is formed on the intermediate transfer belt 12a. The multicolor toner image formed on the intermediate transfer belt 12a is conveyed to a secondary transfer nip portion 15 between the intermediate transfer belt 12a and a secondary transfer roller 16 in accordance with a rotation of the intermediate transfer belt 12a.

A paper feed unit 13 includes a paper feed roller 9, a conveyance roller pair 10, a paper feed cassette 11, and a separation pad 23. A sheet S set by a user is contained in the feed cassette 11. The sheet S may be called recording paper, recording material, recording medium, paper, transfer material, transfer paper, or the like. The paper feed roller 9 feeds the sheet S from the feed cassette 11 to a conveyance path. Note that the sheet S contained in the feed cassette 11 is fed to the conveyance path by the separation pad 23 one sheet at a time. The conveyance roller pair 10 conveys the sheet S fed on the conveyance path toward a registration roller pair 17. When the sheet S is conveyed to the registration roller pair 17, in synchronization with a timing at which the toner image on the intermediate transfer belt 12a reaches the secondary transfer nip portion 15, the sheet S is conveyed to the secondary transfer nip portion 15 by the registration roller pair 17. Thus, the toner image on the intermediate transfer belt 12a is transferred (secondary transfer) onto the sheet S in the secondary transfer nip portion 15.

The sheet S onto which the toner image is transferred is conveyed to a fixing unit 14. The fixing unit 14 includes a fixing belt 14a, a pressure roller 14b, and a belt guide component 14c, and the fixing belt 14a is guided to a belt guide component 14c to which a heat generation device such as a heater is bonded. The fixing nip portion is formed between the fixing belt 14a and the pressure roller 14b. The fixing unit 14 fixes the toner image on the sheet S by applying heat and pressure to the toner image formed on the sheet S in the fixing nip portion. After the fixing process by the fixing unit 14, the sheet S is discharged to a sheet discharge tray 21 by a discharge roller pair 20.

Toner remaining on the photosensitive drum 1 after the primary transfer of the toner image to the intermediate transfer belt 12a is removed from the photosensitive drum 1 by the cleaning blade 8 and collected into a waste toner container in the cleaner unit 5. Also, toner remaining on the intermediate transfer belt 12a after the secondary transfer of the toner image to the sheet S is removed from the intermediate transfer belt 12a by a cleaner unit 22, and then collected in the waste toner container (not shown graphically) via a waste toner conveyance path.

A toner detection unit 31 (optical sensor) is arranged at a position facing the driving roller 12b in the image forming apparatus 100. The toner detection unit 31 can optically detect toner on the intermediate transfer belt 12a as will be described later. The image forming apparatus 100 according to the present embodiment forms a test pattern constituted by a toner image on the intermediate transfer belt 12a, and detects the test pattern formed on the intermediate transfer belt 12a by the toner detection unit 31. Additionally, the image forming apparatus 100 performs a later described calibration based on the result of the detection of the test pattern by the toner detection unit 31.

<Control Configuration of Image Forming Apparatus>

FIG. 2 is a block diagram for illustrating an example configuration of a control system of the image forming apparatus 100 according to the present embodiment. Note that in FIG. 2, only devices necessary for the explanation of the present embodiment are illustrated. The image forming apparatus 100 is equipped with a control unit 41, which incorporates a microcomputer, as an engine control unit. The image forming apparatus 100 further comprises, as devices that are connected to enable communication with the control unit 41, an interface (I/F) board 42, a low voltage power supply 43, the high voltage power supply 44, various drive motors 45, various sensors 46, the exposure unit 3, the paper feed unit 13, the fixing unit 14, and the toner detection unit 31.

The I/F board 42 is capable of communicating with a host computer 40, which is external to the image forming apparatus 100, via a network such as a LAN. The low voltage power supply 43 supplies voltage to the control unit 41 for the control unit 41 to operate. The high voltage power supply 44 supplies, in accordance with control by the control unit 41, a bias voltage to the charging rollers 2, the developing rollers 24, the primary transfer rollers 26, and the secondary transfer roller 16 at a time of image formation execution. Among the various drive motors 45 are included a drive motor for rotating the photosensitive drums 1, a drive motor for rotating the developing rollers 24, and the like. Among the various sensors 46 are included sensors other than the toner detection unit 31 such as a sensor for detecting a sheet S conveyed along the conveyance path. The control unit 41, by controlling the various devices illustrated in FIG. 2 based on various signals such as an output signal of the toner detection unit 31, output signals of the various sensors 46, or the like, executes various control such as sequence control for calibration of the image forming apparatus 100 and image formation.

<Calibration of Image Forming Apparatus>

Figure 3:
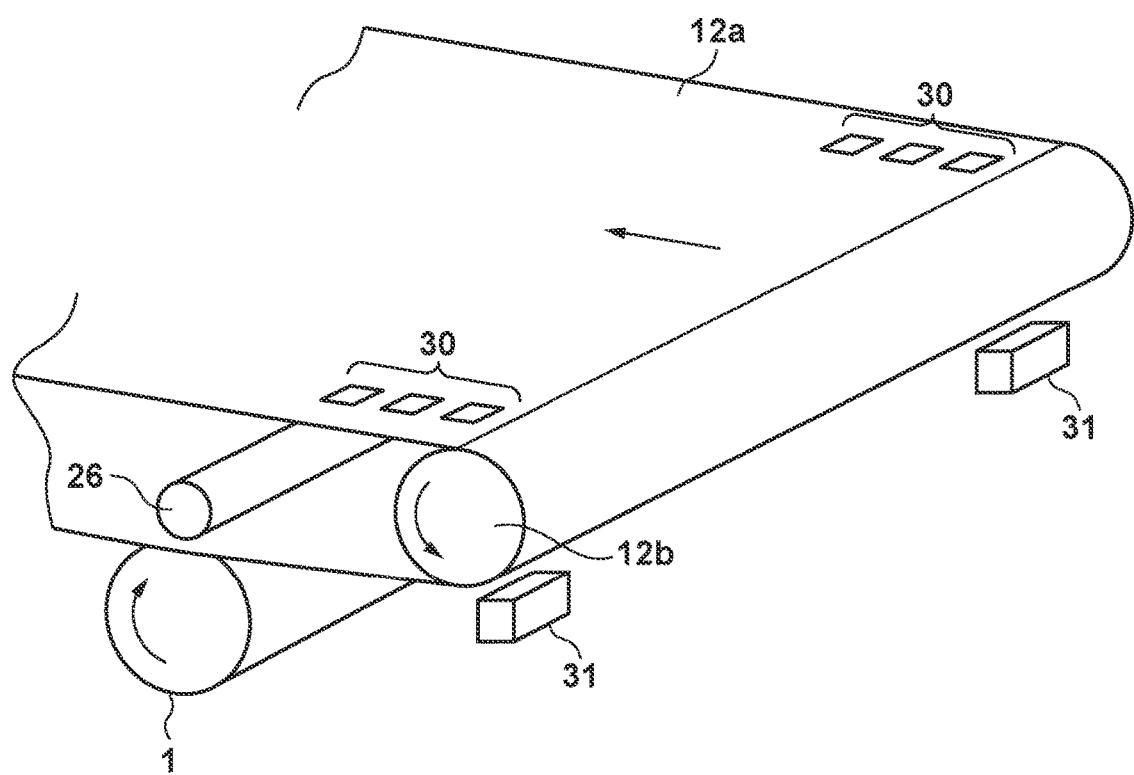
FIG. 3 is a perspective view illustrating an arrangement example of a toner detection unit in relation to an intermediate transfer belt.

Next, with reference to FIG. 3, a calibration of the image forming apparatus 100 (automatic correction control) will be described. FIG. 3 is a perspective view illustrating an arrangement example of the toner detection unit 31 in relation to the intermediate transfer belt 12a, and illustrates an example of a state of the intermediate transfer belt 12a at a time of calibration execution. Broadly divided, the calibration of the image forming apparatus 100 includes two kinds of control: "color misregistration correction control" and "image density control". These two kinds of control are both performed by forming a test pattern 30 on the intermediate transfer belt 12a while the image forming apparatus 100 is not performing image formation to a sheet S, and optically detecting the formed test pattern 30 by the toner detection unit 31.

If the test pattern 30 is detected by the toner detection unit 31 on a flat portion of the intermediate transfer belt 12a, it is difficult to obtain satisfactory sensor output due to vibration and the like at the time of belt movement. Accordingly, the toner detection unit 31 is arranged at a position facing the driving roller 12b via the intermediate transfer belt 12a as illustrated in FIG. 3 rather than at a position facing the flat portion of the intermediate transfer belt 12a. The test pattern 30 formed on the surface (outer surface) of the intermediate transfer belt 12a is detected by the toner detection unit 31 at a position facing the driving roller 12b when it passes the position of the driving roller 12b. Also, so that it is possible to detect the test pattern 30 at least two positions in a direction orthogonal to the movement direction of the surface of the intermediate transfer belt 12a, at least two toner detection unit 31 are arranged in such an orthogonal direction. Below, both the color misregistration correction control and the image density control will be described more specifically.

(Color Misregistration Correction Control)

The color misregistration correction control corresponds to color misregistration correction control in which an amount of relative positional misalignment (color misregistration) between the image forming stations for toner images formed by the respective image forming stations is measured, and correction of the color misregistration is performed based on the measurement results. The control unit 41 performs a color misregistration correction control by adjusting the timing at which each line is started to be written in addition to controlling the exposure units 3 so that a scanning speed and an amount of exposure light of laser beam on the photosensitive drums 1 becomes a predetermined speed and a predetermined amount of light.

For example, if the exposure unit 3 is of a polygon mirror type, the control unit 41, upon image formation, generates an image top signal by counting write start reference pulses from the exposure unit 3, and outputting the generated image top signal to the I/F board 42. The I/F board 42 outputs, in synchronization with the image top signal, exposure data one line at a time (one surface of a polygon mirror) to the exposure unit 3 via the control unit 41. By causing the output timing of the image top signal from the control unit 41 to change by an amount of time corresponding to a few dots for each image forming station, it is possible to cause the timing at which each line is started to be written to change by a few dots. With this, it is possible to adjust an image write start position in the main scanning direction of the photosensitive drum 1. Also, by causing the write timing to change in units of lines, it is possible to cause the whole image to shift in a conveyance direction (a sub scanning direction) of the toner image on the photosensitive drum 1. With this, it is possible to adjust an image write start position in the sub scanning direction of the photosensitive drum 1. Also, by controlling a difference in a rotational phase of the polygon mirror of the exposure unit 3 between the image forming stations, it is possible to perform alignment of the images of the respective colors in the sub scanning direction at a resolution of one line or less. Furthermore, it is possible to perform correction of a main-scanning magnification by causing the clock frequency to be used as the reference of ON/OFF in the exposure data to change.

In this way, correction of a color misregistration between image forming stations in the color misregistration correction control can be realized by adjusting a reference clock and an image formation timing. To realize the color misregistration correction control, it is necessary to measure the relative color misregistration amounts between the image forming stations as described above. In the color misregistration correction control, a test pattern for a color misregistration amount measurement of at least two columns on the intermediate transfer belt 12a is formed for each color, and positions (a time of passage of a position facing the optical sensor) of the test pattern are detected by at least two optical sensors (the toner detection unit 31). The control unit 41, based on the results of this detection, calculates a relative color misregistration amount in the main scanning direction and the sub scanning direction between the image forming stations, a magnification factor of the main scanning direction, and a relative tilt. Furthermore, the control unit 41 performs a color misregistration correction as described above so that the color misregistration amount between the image forming stations becomes small.

(Image Density Control)

Image density control is control for correcting an image forming condition so that a density characteristic of an image formed by the image forming apparatus 100 becomes a desired density characteristic. In the image forming apparatus 100, due to temperature and humidity conditions and the levels of usage of the image forming stations of the respective colors, a density characteristic of formed images (toner images) changes. Image density control is performed to correct these changes. Specifically, the test pattern 30 is formed on the intermediate transfer belt 12a, and based on the result of detection of the test pattern 30 by the toner detection unit 31, an image forming condition is adjusted so as to obtain a desired density characteristic. Note that the test pattern 30 may be generated by the control unit 41, or may be generated by an external apparatus (for example, the host computer 40).

The control unit 41 (CPU) calculates (detects a density of a toner image) a value corresponding to a density of the toner image which is the test pattern 30 from a received light amount signal after A/D (analog/digital) conversion which is outputted from the toner detection unit 31. Furthermore, the control unit 41, based on the result of the detection of the density of the toner image, sets the image forming condition to be used when performing image formation. The image forming condition that is set is a charge bias voltage, a developing bias voltage, an amount of exposure light (the laser power of the exposure unit 3), or the like, for example. By repeating such settings, it is possible to optimize an image forming condition related to an image density characteristic. Note that the control unit 41 stores in a memory within the control unit 41 the image forming condition that has been set, so as to be able to use it at a time of image formation and at a time of the next image density control.

By performing such image density control, it is possible to adjust the maximum density of each color to a desired value, and it is possible to prevent the occurrence of an image defect called "fogging" in which unwanted toner adheres to a white background portion of an image. Also, by performing the image density control, it is possible to keep fixed the color balance of the respective colors, and to prevent an image defect and a fixing defect due to excessive application of toner.

<Configuration of Toner Detection Unit>

Figure 4:
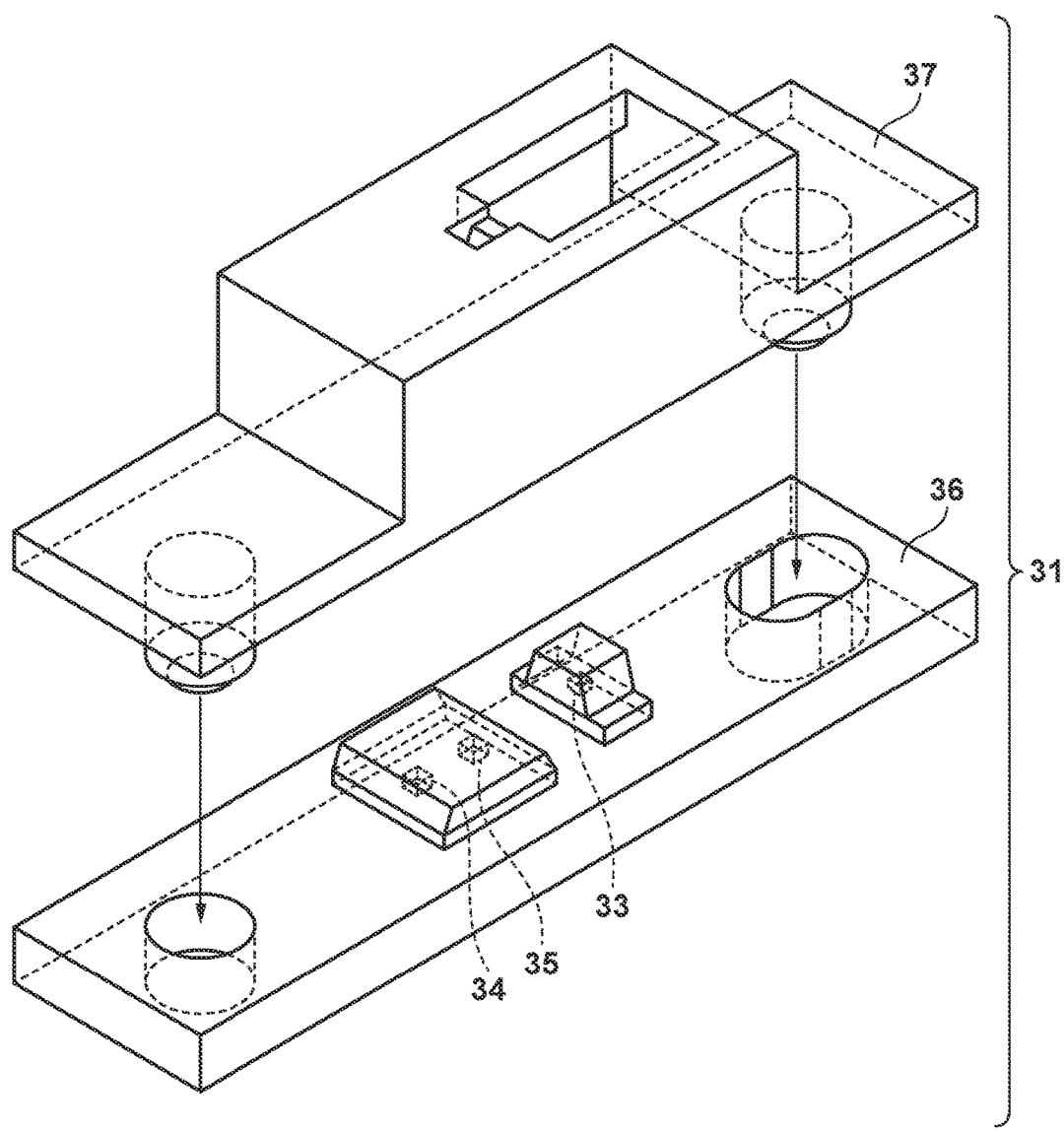
FIG. 4 is a perspective view illustrating an example configuration of the toner detection unit.
Figure 5A:
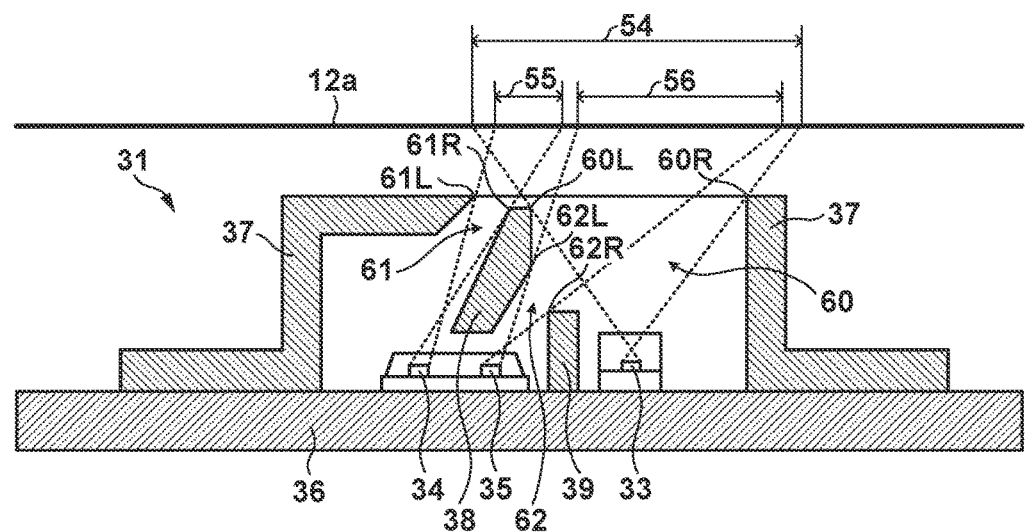
FIG. 5A and FIG. 5B are cross-sectional views illustrating an example configuration of the toner detection unit.
Figure 5B:
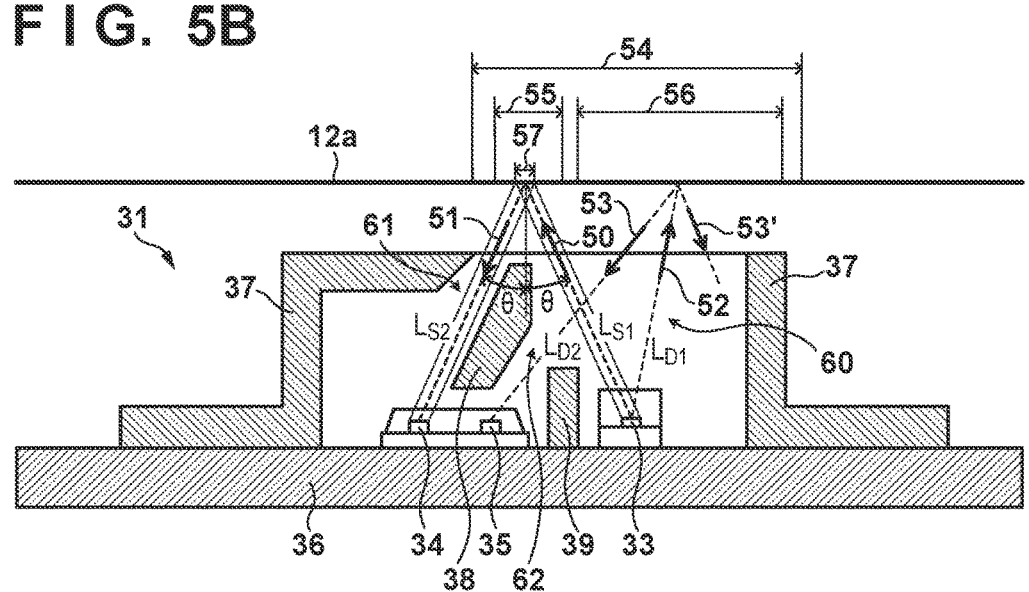

Next, a configuration of the toner detection unit 31 which is for detecting the test pattern 30 is described. FIG. 4, and FIGS. 5A and 5B are respectively a perspective view and an outline cross-sectional view illustrating an example configuration of the toner detection unit 31. The toner detection unit 31, as illustrated in FIG. 4, has a configuration in which a housing 37 is fixed to a circuit board 36 by projecting portions of the housing 37 being inserted into holes arranged in the circuit board 36. FIGS. 5A and 5B illustrate states in which the housing 37 is fixed in relation to the circuit board 36.

The toner detection unit 31 comprises an LED 33 (a light emitting element) and two light receiving elements 34 and 35 as optical elements. The LED 33 irradiates light towards the intermediate transfer belt 12a which is an irradiated member. That is, the LED 33 irradiates light towards the intermediate transfer belt 12a after the toner, which is the detection target (measurement target object), has been attached. The light receiving elements 34 and 35 are used to respectively receive the specular reflection light and the diffused reflection light of the light that the LED 33 irradiated toward the intermediate transfer belt 12a. In the toner detection unit 31, the housing 37 is configured to respectively guide, to the light receiving elements 34 and 35, the specular reflection light and the diffused reflection light of the light that the LED 33 irradiated to the intermediate transfer belt 12a.

The LED 33 and the two light receiving elements 34 and 35 are directly mounted on the surface (mounting surface) of the same circuit board 36, and are mounted in a line on the circuit board 36. The light receiving elements 34 and 35, which respectively receive the specular reflection light and the diffused reflection light of light that the LED 33 irradiates toward the intermediate transfer belt 12a, are arranged beside each other on the circuit board 36. In the present embodiment, the light receiving element 34 is arranged at a position more separated from the LED 33 than the light receiving element 35, and the light receiving element 35 is arranged at a position closer to the LED 33 than the light receiving element 34. Also, as illustrated in FIGS. 5A and 5B, a light shielding wall 39 to prevent light emitted from the LED 33 from being received directly by the light receiving element 35 is provided between the LED 33 and the light receiving element 35.

Figure 6:
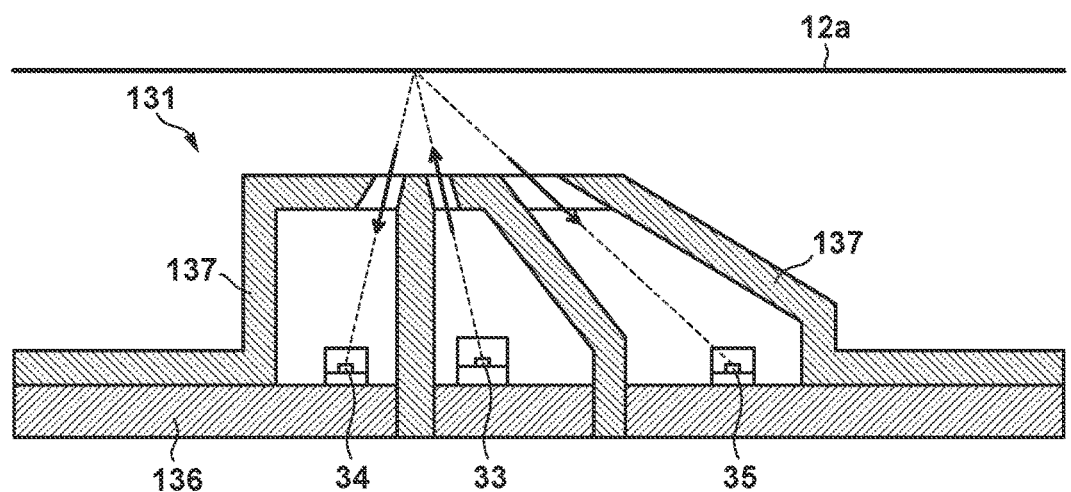
FIG. 6 is a perspective view illustrating an example configuration of the toner detection unit which is a first comparative example.

The light receiving elements 34 and 35 of the present embodiment is configured by an integrated circuit (IC) in which phototransistors (semiconductors) having a sensitivity to wavelengths of light emitted from the LED 33 are integrated and COB-mounted on a substrate. In this way, it is possible to configure the light receiving elements 34 and 35 being integrated in an integrated circuit by arranging the light receiving elements 34 and 35 on the same side (one side of the LED 33) with respect to the LED 33 in an arrangement direction of the light receiving elements 34 and 35 and the LED 33. With this, it is possible to miniaturize the toner detection unit 31 in the arrangement direction. While specifics are described later, in a toner detection unit 131 of FIG. 6, the light receiving element 34 and the light receiving element 35 are arranged on different sides (both sides of the LED 33) with respect to the LED 33 in the arrangement direction. Because in the toner detection unit 31 in the present embodiment of FIG. 5A and FIG. 5B, the light receiving elements 34 and 35 are integrated in an integrated circuit in contrast to the toner detection unit 131, it can be seen that miniaturization is achieved in the arrangement direction. The phototransistors mounted on the substrate are covered by a transmissive resin material. The substrate on which the light receiving elements 34 and 35 are mounted is arranged on the circuit board 36. The LED 33 (light emitting element) and the light receiving elements 34 and 35 of the present embodiment use infrared light. However, a light emitting element and light receiving elements that use light of other wavelengths may be used in the toner detection unit 31 if the light is of a wavelength to which the light receiving elements are sensitive depending on the combination of the light emitting element and the light receiving elements. Also, in place of phototransistors, photodiodes may be used as the light receiving elements 34 and 35.

As illustrated in FIG. 5A, a light guiding path 60 is provided in the housing 37 of the toner detection unit 31 to guide light emitted from the LED 33 toward the intermediate transfer belt 12a. Light guiding paths 61 and 62 are further provided in the housing 37 to guide reflected light of the light emitted from the LED 33 to the light receiving elements 34 and 35. The light guiding paths 60 and 61 are configured by openings arranged in the housing 37, and are separated by a light shielding wall 38. Also, the light guiding path 62 is configured by the light shielding wall 38 and the light shielding wall 39, and is separated from the light guiding path 61 by the light shielding wall 38. Note that, within the housing 37, the light guiding path 62 overlaps a portion of the light guiding path 60 which guides light emitted from the LED 33 towards the intermediate transfer belt 12a, which is the irradiated member, and this contributes to the miniaturization of the toner detection unit 31.

The light shielding wall 38 is arranged so that the diffused reflection light from a light-receivable region 55 (which is described later) is not received by the light receiving element 35 (so that the diffused reflection light is not incident on the light receiving element 35 through the light guiding path 62). The light shielding wall 38 is formed integrally in the housing 37, is arranged above, in a vertical direction in relation to the mounting surface of the circuit board 36, the position of the light receiving element 35 on the mounting surface (that is, immediately above the light receiving element 35), and is formed close to the opening of the housing 37.

(Irradiation Region 54 of Light from the LED 33)

Here, the irradiation region 54 of the light from the LED 33 as illustrated in FIG. 5A corresponds to a region in which light from the LED 33 is irradiated on the outer surface of the intermediate transfer belt 12a (on the irradiated member). The irradiation region 54 is defined by a straight line connecting a left corner 60L of the light guiding path 60 and one edge of the LED 33, and a straight line connecting a right corner 60R of the light guiding path 60 and the other edge of the LED 33.

(Light-Receivable Regions 55 and 56 for the Light Receiving Elements 34 and 35)

The light-receivable region 55 (second region) for the light receiving element 34 illustrated in FIG. 5A corresponds to a region (range), within the irradiation region 54, in which light that the light receiving element 34 can receive is irradiated by the LED 33, and is a region that is a portion of the irradiation region 54. The light-receivable region 55 is defined by a straight line connecting a left corner 61L of the light guiding path 61 and one edge of the light receiving element 34 and a straight line connecting a right corner 61R of the light guiding path 61 and the other edge of the light receiving element 34.

The light-receivable region 56 (first region) of the light receiving element 35 illustrated in FIG. 5A corresponds to a region (range), within the irradiation region 54, in which light that the light receiving element 35 can receive is irradiated by the LED 33, and is a region that is a portion of the irradiation region 54. The light-receivable region 56 is defined by a straight line connecting a left corner 62L of the light guiding path 62 and one edge of the light receiving element 35 and a straight line connecting a right corner 62R of the light guiding path 62 and the other edge of the light receiving element 35.

In the present embodiment, as illustrated in FIG. 5A, the housing 37 is configured to guide the specular reflection light from the light-receivable region 55 within the irradiation region 54 of the LED 33 to the light receiving element 34, and to guide the diffused reflection light from the light-receivable region 56 within the irradiation region 54 to the light receiving element 35. Also, the housing 37 is configured so that the light-receivable region 55 and the light-receivable region 56 are mutually different regions. Note that the light-receivable region 55 and the light-receivable region 56 are not regions that overlap each other in the present embodiment, but they may partially (for example, edges of each region) overlap.

In the toner detection unit 31, the specular reflection light that the light receiving element 34 receives among the light emitted from the LED 33, as illustrated in FIG. 5B, is light that travels in a direction along an optical axis line 50 in the light guiding path 60, and that is irradiated on the outer surface of the intermediate transfer belt 12a. The specular reflection light from the outer surface of the intermediate transfer belt 12a travels in a direction along an optical axis line 51 approximately, is guided within the light guiding path 61 of the housing 37, reaches the light receiving element 34 and is received. More specifically, the light receiving element 34 receives, among the light irradiated from the LED 33, light (specular reflection light) that is incident at an incident angle θ in a region 57 within the light-receivable region 55 and that is reflected at a reflection angle θ, as well as diffused reflection light of the light that is incident on the light-receivable region 55.

Meanwhile, if the test pattern 30, which is a toner image, is present in the irradiation region 54 on the outer surface of the intermediate transfer belt 12a, light emitted from the LED 33 is specularly reflected by the outer surface of the intermediate transfer belt 12a and is diffusely reflected by the test pattern 30. A portion of such reflected light is reflected in a direction along the optical axis line 51, reaches the light receiving element 34 and is received, and another portion is reflected in a direction along an optical axis line 53, passes through the light guiding path 62, reaches the light receiving element 35 and is received.

In the present embodiment, as illustrated in FIG. 4 and FIGS. 5A and 5B, by mounting the two light receiving elements 34 and 35 as an IC on the circuit board 36, miniaturization of the toner detection unit 31 over what was conventional is realized. Here, in FIG. 6, a cross-sectional view illustrating a configuration of the toner detection unit 131 is illustrated as a comparative example (first comparative example) in contrast to the present embodiment. In the toner detection unit 131 illustrated in FIG. 6, two light receiving elements 34 and 35 that respectively receive the specular reflection light and the diffused reflection light of light emitted from the LED 33 (light emitting element) are mounted on a circuit board 136 as independent circuit elements. Also, in conformity with this kind of mounting, separate openings corresponding to the LED 33 and the two light receiving elements 34 and 35 are provided on a housing 137. In the toner detection unit 31 of the present embodiment, it is possible to miniaturize a size of a direction (horizontal direction in FIG. 6) in which the LED 33 and the two light receiving elements 34 and 35 are arranged over the toner detection unit 131 illustrated as the comparative example.

Also, when using the toner detection unit 31 of the present embodiment, it is possible to detect toner images (the test pattern 30) simultaneously in two different regions (light-receivable regions 55 and 56) on the intermediate transfer belt 12a. For example, the toner detection unit 31 is arranged so that the two light receiving elements 34 and 35 are arranged in a direction orthogonal to a movement direction of the surface of the intermediate transfer belt 12a. In such a case, the light-receivable regions 55 and 56 for the light receiving elements 34 and 35 are arranged in a direction orthogonal to the movement direction of the surface of the intermediate transfer belt 12a. As a result, when the toner detection unit 31 is used, it is possible to detect the toner images (the test pattern 30) which respectively passes through the light-receivable region 55 and the light-receivable region 56 at a timing when the rotational phases of the intermediate transfer belt 12a are the same phase. In second through fifth embodiments, examples of detection of the test pattern 30 that use such a feature of the toner detection unit 31, and control based on the result of such detection are illustrated.

Note that it is possible to employ, in the toner detection unit 31 of the present embodiment, light receiving elements for which toner detection precision differs between a low density side and a high density side. For example, configuration may be such that while the light receiving element 34 which receives specular reflection light has a high detection precision on the low density side, the light receiving element 35 which receives diffused reflection light has a high detection precision on the high density side. Even in such a case, it is possible to enhance toner detection precision by using both the light reception result of the specular reflection light by the light receiving element 34 and the light reception result of the diffused reflection light by the light receiving element 35 in the toner detection unit 31 of the present embodiment.

<Toner Detection Unit Characteristics>

Below, characteristics of toner detection by the toner detection unit 31 of the present embodiment are described. Firstly, the received light amount and the optical path length of the light receiving elements 34 and 35, a reflection characteristic of the intermediate transfer belt 12a, and a comparative example, which are necessary for the explanation of toner detection characteristics, will be described.

(Received Light Amounts and Optical Path Length of Light Receiving Elements)

Generally, the received light amounts, which are intensities (light amounts) of light that the light receiving elements 34 and 35 receive, are proportional to the light receiving area and inversely-proportional to the square of the length of the light path that light passes through (optical path length).

Accordingly, in the present embodiment, the received light amounts of the light receiving elements 34 and 35 are proportional to the areas of the light-receivable regions 55 and 56 for the respective light receiving elements, and inversely-proportional to the squares of the optical path lengths.

As illustrated in FIG. 5B, the optical path length of the light that is emitted from the LED 33 and received by the light receiving element 34 can be expressed as the sum of the distance LS1 from the center of a light-emitting portion of the LED 33 to the center of the light-receivable region 55 and the distance LS2 from the center of the light-receivable region 55 to the center of the light-receiving surface of the light receiving element 34. On the other hand, the optical path length of the light that is emitted from the LED 33 and received by the light receiving element 35 can be expressed as the sum of the distance LD1 from the center of a light-emitting portion of the LED 33 to the center of the light-receivable region 56 and the distance LD2 from the center of the light-receivable region 56 to the center of the light-receiving surface of the light receiving element 35. That is, the optical path length of the light received by the light receiving element 34=LS1+LS2, and the optical path length of the light received by the light receiving element 35=LD1+LD2.

(Reflection Characteristic of Intermediate Transfer Belt)

Figure 7A:
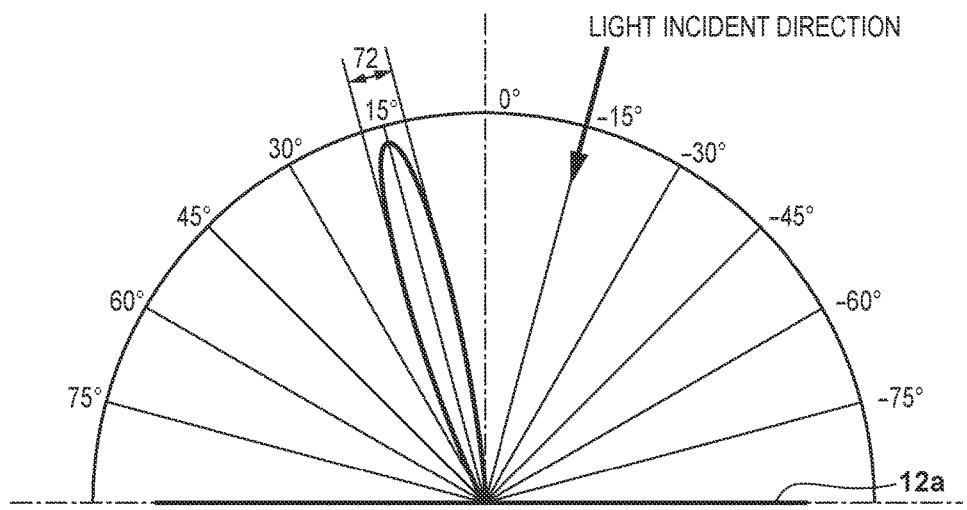
FIG. 7A and FIG. 7B illustrates examples of a reflection directivity characteristic of the intermediate transfer belt.
Figure 7B:
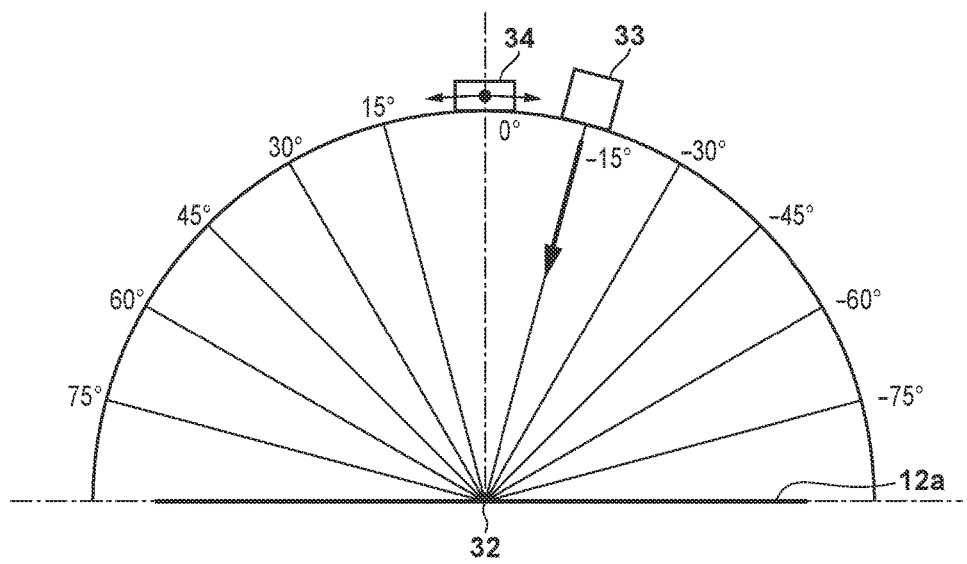

FIGS. 7A and 7B illustrate examples of a reflection directivity characteristic of the intermediate transfer belt 12a. FIG. 7A illustrates a measurement result of a reflection directivity characteristic, and FIG. 7B illustrates a concept of a method of measuring the reflection directivity characteristic. In this measurement, as illustrated in FIG. 7B, a vertical direction in relation to the outer surface of the intermediate transfer belt 12a is assumed to be 0°, and light is irradiated from the LED 33 (light emitting element) which is arranged as a point light source at a position rotated −15° from the vertical direction, to the intermediate transfer belt 12a. Furthermore, output values of the light receiving element 34 are measured in cases where the light receiving element 34 is caused to rotationally move from a position of −90° to a position of 90° while keeping the distance to the light receiving element 34 from an irradiation point (point on the irradiated surface) 32 where light emitted from the LED 33 is irradiated, to an approximate distance.

FIG. 7A illustrates a reflection directivity characteristic obtained by such a measurement. As illustrated in FIG. 7A, while a specular reflection component is dominant in the reflection characteristic of the intermediate transfer belt 12a, there is a diffused reflection component of an angle width 72 that is centered in the specular reflection direction. That is, the intermediate transfer belt 12a has a diffused reflection characteristic in which there is a diffused reflection component having a high intensity in the specular reflection direction.

Comparative Example

Figure 8:
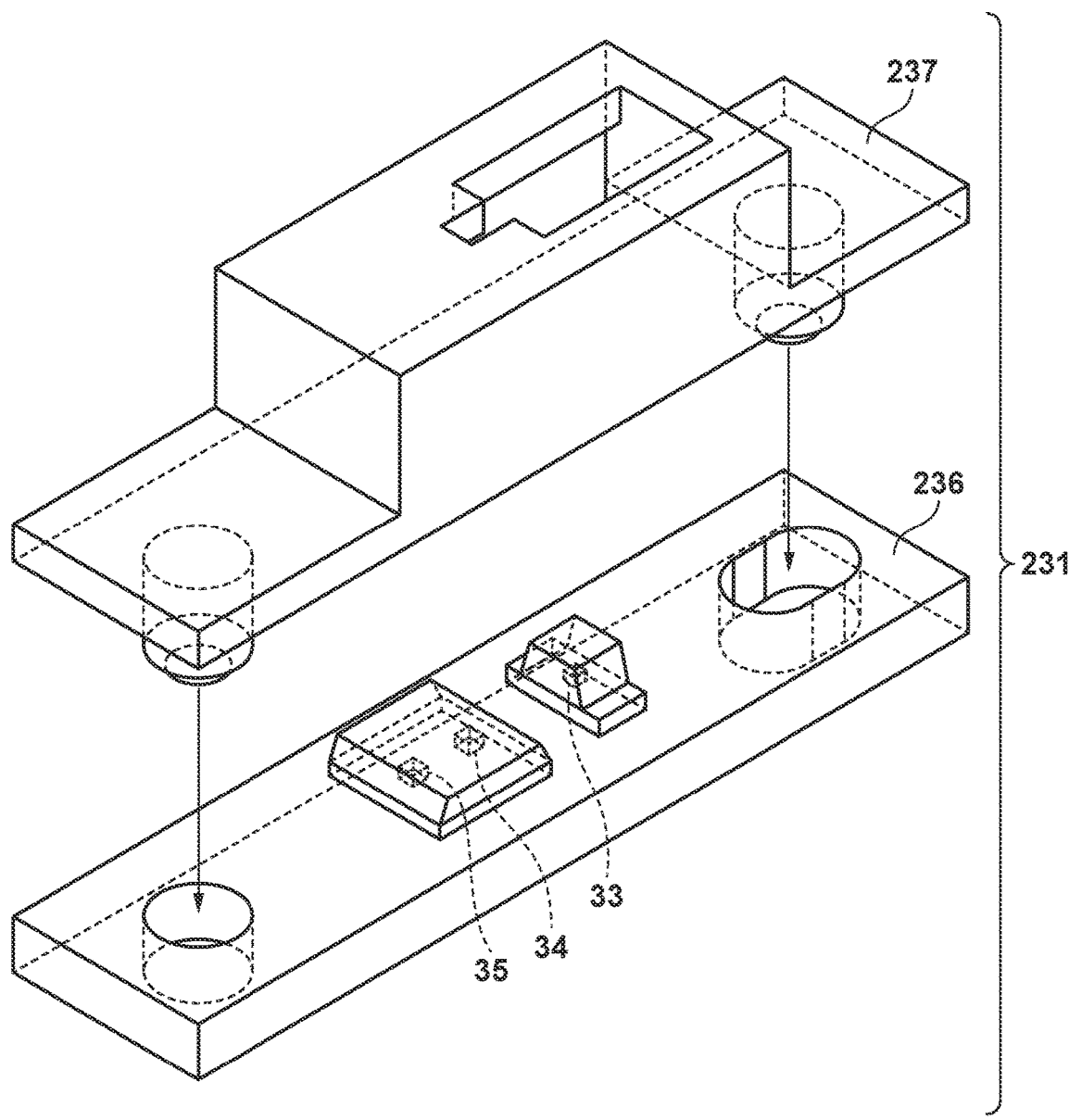
FIG. 8 is a perspective view illustrating a configuration of the toner detection unit which is a second comparative example.
Figure 9A:
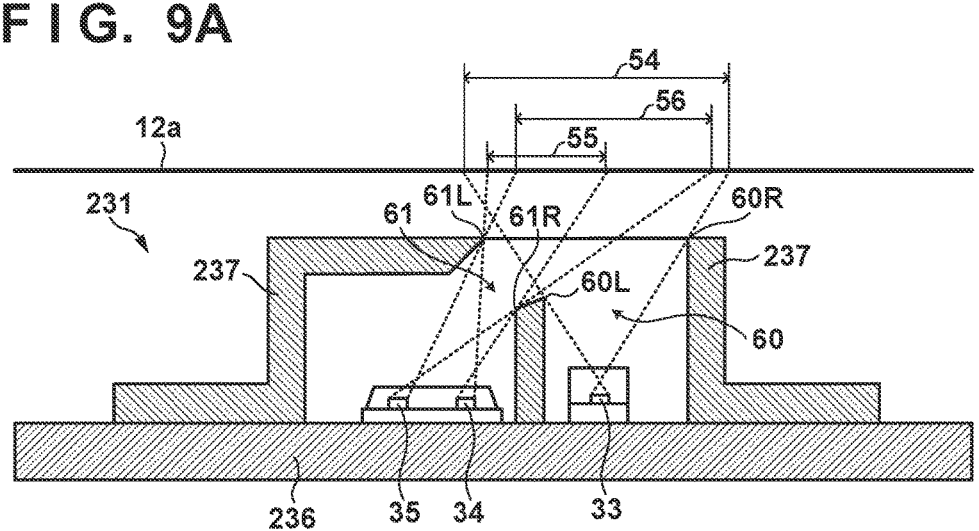
FIG. 9A and FIG. 9B are cross-sectional views illustrating a configuration of the toner detection unit which is the second comparative example.
Figure 9B:
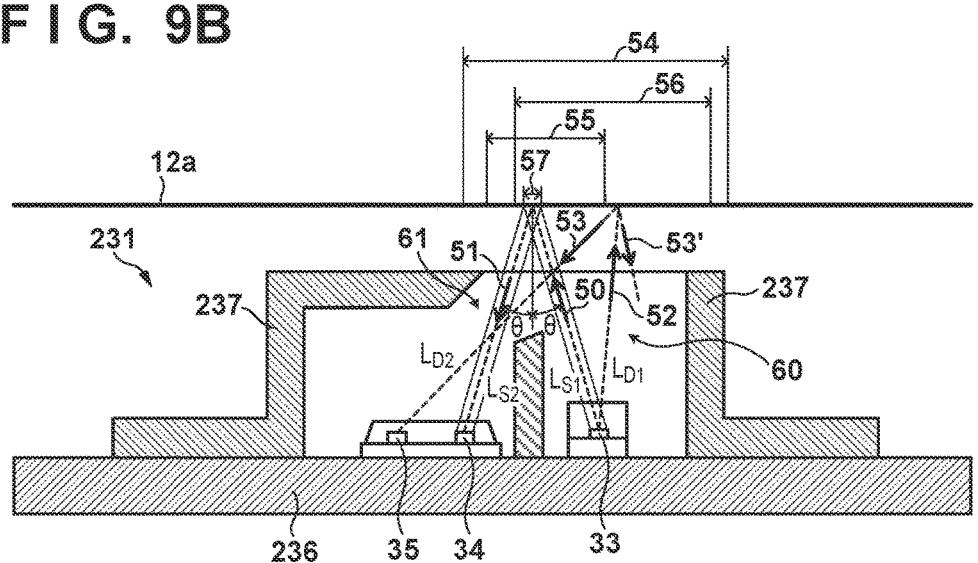

FIG. 8, and FIGS. 9A 9B are respectively a perspective view and an outline cross-sectional views illustrating a configuration of a toner detection unit 231, which is illustrated as a comparative example (second comparative example) in contrast to the present embodiment. In the toner detection unit 231 illustrated in FIG. 8 and FIGS. 9A 9B, the LED 33 (light emitting element) and the two light receiving elements 34 and 35 are directly mounted to the surface of the same circuit board 236, and are arranged in a line on the circuit board 236. The light receiving elements 34 and 35 of the toner detection unit 231, similarly to the light receiving elements 34 and 35 of the toner detection unit 31 of the present embodiment, are configured to respectively receive specular reflection light and diffused reflection light of light that the LED 33 irradiates toward the intermediate transfer belt 12a.

However, the configuration of the toner detection unit 231 of the comparative example differs to the configuration of the toner detection unit 31 of the present embodiment in that the arrangement of the light receiving elements 34 and 35 is opposite to the arrangement illustrated in FIG. 4 and FIGS. 5A and 5B. That is, in the toner detection unit 231, the light receiving element 34 is arranged at a position closer to the LED 33 than the light receiving element 35, and the light receiving element 35 is arranged at a position more separated from the LED 33 than the light receiving element 34. Note that an opening depending on the arrangement of the LED 33 and the light receiving elements 34 and 35 is formed in a housing 237 of the toner detection unit 231 so that the light receiving elements 34 and 35 can respectively receive the specular reflection light and the diffused reflection light of light emitted from the LED 33.

(Toner Detection Characteristic)

Next, a toner detection characteristic of the toner detection unit 31 of the present embodiment is described, where a toner detection characteristic of the toner detection unit 231 illustrated in FIG. 8 and FIGS. 9A and 9B is made to be a comparison target. FIGS. 10A to 10D illustrate examples of output of the light receiving elements 34 and 35 in cases where toner images having different densities are formed in order on the intermediate transfer belt 12a as the test pattern 30, and the formed test pattern 30 is detected by the toner detection unit 31. FIGS. 10A and 10B respectively illustrate output of the light receiving elements 34 and 35 of the toner detection unit 31 of the present embodiment. FIGS. 10C and 10D respectively illustrate output of the light receiving elements 34 and 35 of the toner detection unit 231 of the comparative example obtained in cases when similar measurement to that for the toner detection unit 31 of the present embodiment is performed.

Here, the toner detection unit 31 is positioned within the image forming apparatus 100 so that the light receiving elements 34 and 35 are arranged in a direction orthogonal to the movement direction of the surface of the intermediate transfer belt 12a which the toner detection unit 31 faces. In such a case, the light-receivable regions 55 and 56 for the light receiving elements 34 and 35 are arranged in the direction orthogonal to the movement direction of the surface of the intermediate transfer belt 12a. The light receiving elements 34 and 35 receive light reflected from the light-receivable regions 55 and 56, and generate and output detection signals of values corresponding to the received light amounts. Note that the movement direction of the surface of the intermediate transfer belt 12a, and the direction orthogonal to the movement direction respectively correspond to the sub-scanning direction and the main scanning direction in scanning of the photosensitive drum 1 by a laser beam. In FIGS. 10A to 10D, measurement results of output of the light receiving elements 34 and 35 that are obtained by forming the test pattern 30 in a range that is equal to or wider than the irradiation region 54 in the main scanning direction are illustrated. That is, configuration is such that the same test pattern is detected by the light receiving elements 34 and 35 when the test pattern 30 passes through the light-receivable regions 55 and 56.

FIGS. 10A to 10D illustrate changes in output of the light receiving elements 34 and 35 in cases where the test pattern 30 is formed on the intermediate transfer belt 12a such that the density of the toner gradually increases 20% at a time from 0% to 100% and is detected by the toner detection unit 31. In each of the graphs of FIGS. 10A to 10D, the density [%] of toner (that is the detection target) that passes through the light-receivable regions 55 and 56 for the light receiving elements 34 and 35 is recorded. The output values 101 and 102 corresponding to the density 0% are equivalent to output values in cases where a toner image is not formed on the light-receivable regions 55 and 56 and the light receiving elements 34 and 35 respectively receive reflected light from the surface (outer surface) of the intermediate transfer belt 12*a*.

Firstly, FIG. 10A illustrates output of the light receiving element 34 that receives specular reflection light of light emitted from the LED 33 in the toner detection unit 31 of the present embodiment. The output value of the light receiving element 34 becomes a maximum value (output value 101) in a case where light reflected from the surface of the intermediate transfer belt 12*a* on which the test pattern 30 is not formed is received. This is because, as explained using FIGS. 7A and 7B, while the intermediate transfer belt 12*a* has somewhat of the diffused reflection characteristic as an optical characteristic, the specular reflection characteristic is dominant. Also, the output value of the light receiving element 34 becomes lower as the density of the toner increases if reflected light is received from the test pattern 30 (the toner image). This is because the more the density of the toner increases, the less the light amount of the specular reflection light from the toner becomes due to the diffused reflection characteristic of the toner.

It can be seen that while the output of the light receiving element 34 illustrated in FIG. 10A shows a similar tendency as compared to the output of the light receiving element 34 of the comparative example illustrated FIG. 10C, the values overall are slightly smaller than in the comparative example. Such a difference in output values depends on the optical path lengths (LS1+LS2) of the light that the light receiving element 34 receives. Specifically, when the configuration of the toner detection unit 31 illustrated in FIG. 5B and the configuration of the comparative example illustrated in FIG. 9B are compared, in the configuration of the present embodiment the distance between the LED 33 and the light receiving element 34 is greater than in the configuration of the comparative example, and the incident angle (reflection angle) θ is larger than in the configuration of the comparative example. Accordingly, in the configuration of the present embodiment, the optical path length (LS1+LS2) is longer than in the configuration of the comparative example, resulting in a difference in output of the light receiving element 34.

However, as illustrated in FIGS. 10A and 10C, such a difference in output of the light receiving element 34 is small. This is because the specular reflection light that the light receiving element 34 receives has a comparatively high directivity, and so the difference in the received light amount of the specular reflection light that arises due to the difference in the optical path length is small. The toner detection unit 31 of the present embodiment, as described above, has a characteristic in which the output of the light receiving element 34 becomes slightly smaller compared to the toner detection unit 231 of the comparative example, but has a sufficient toner detection characteristic. Specifically, as illustrated in FIG. 10A, there exists a sufficient difference between the output value 101 (the maximum value) in the case where the light receiving element 34 receives light reflected from the surface of the intermediate transfer belt 12*a* and the output values in the cases where the light receiving element 34 receives light reflected from toner images of respective densities. Accordingly, if using the toner detection unit 31 of the present embodiment, it is possible to determine the existence or absence of toner (in the light-receivable region 55) on the intermediate transfer belt 12*a* and the density of the toner at a sufficient precision by comparison processing between the output value of the light receiving element 34 and a threshold value.

Next, FIG. 10B illustrates output of the light receiving element 35 that receives diffused reflection light of light emitted from the LED 33 in the toner detection unit 31 of the present embodiment. The output of the light receiving element 35 is shown to change in an opposite tendency to that of the output of the light receiving element 34 (FIG. 10A) with respect to the change in toner density. Specifically, the output value of the light receiving element 35 becomes a minimum value (output value 102) in a case where light reflected from the surface of the intermediate transfer belt 12*a* on which the test pattern 30 is not formed is received. This is because the diffused reflection characteristic of the intermediate transfer belt 12*a* is weak. Also, the output value of the light receiving element 35 becomes higher as the density of the toner increases if reflected light is received from the test pattern 30 (the toner image). This is because the more the density of the toner increases, the greater the light amount of the diffused reflection light from the toner becomes due to the diffused reflection characteristic of the toner.

When the output of the light receiving element 35 illustrated in FIG. 10B is compared to the output of the light receiving element 35 of the comparative example illustrated in FIG. 10D, it can be seen that while the maximum value is larger than the comparative example, the minimum value (the output value 102) is smaller, that is, the difference 103 between the minimum value and the maximum value is larger than in the comparative example. Also, in the present embodiment, compared to the comparative example, there exists a larger difference between the output value 102 (minimum value) in the case where the light receiving element 35 receives light reflected from the surface of the intermediate transfer belt 12*a* and the output values in the cases where the light receiving element 35 receives light reflected from toner images of respective densities. Accordingly, if using the toner detection unit 31 of the present embodiment, it is possible to determine the existence or absence of toner (in the light-receivable region 56) on the intermediate transfer belt 12*a* and the density of the toner at higher precision than in the comparative example by comparison processing between the output value of the light receiving element 35 and a threshold value.

Next, a reason that a difference in output of the light receiving element 35 that receives diffused reflection light of light emitted from the LED 33 occurs (that is, a difference in the toner detection characteristic arises) between the toner detection unit 31 of the present embodiment and the toner detection unit 231 of the comparative example is described.

Firstly, a difference between the output value 102 illustrated in FIG. 10B and the output value 102 illustrated in FIG. 10D in a case where the test pattern 30 is not formed on the irradiation region 54 of the LED 33 (the light-receivable region 56) is described. In the configuration of the comparative example illustrated in FIG. 9B, the light receiving element 35 is configured to receive both the diffused reflection light that travels in the specular reflection direction approximately along the optical axis line 51, and the diffused reflection light that travels in a direction along the optical axis line 53. For the diffused reflection light that travels along the optical axis line 53, the optical path length is comparatively long (LD1+LD2), and it is received by the light receiving element 35 at a low intensity. Meanwhile, for the diffused reflection light which travels in the specular reflection direction, not only is the optical path length comparatively shorter (LS1+LS2), it is received by the light receiving element 35 at a comparatively high intensity due to the foregoing diffused reflection characteristic of the intermediate transfer belt 12a. Accordingly, as illustrated in FIG. 10D, the output value 102 of the light receiving element 35 in the toner detection unit 231 of the comparative example increases by an amount corresponding to the received light amount of light reflected from the surface of the intermediate transfer belt 12a. This means that, in the output of the light receiving element 35, the amplitude component effective for the detection of toner becomes smaller.

In contrast to this, in the configuration of the present embodiment illustrated in FIG. 5B, the light receiving element 35 is configured to receive the diffused reflection light that travels in the direction along the optical axis line 53, and not receive the diffused reflection light that travels in the specular reflection direction approximately along the optical axis line 51. Specifically, the diffused reflection component of the light that travels along the optical axis line 50 from the LED 33 and is reflected at the surface of the intermediate transfer belt 12a in the direction along the optical axis line 51 is blocked by the light shielding wall 38, and is not incident on the light receiving element 35. Also, the comparatively high intensity diffused reflection component of reflected light of the light that has traveled along the optical axis line 52 from the LED 33 travels in a direction of an optical axis line 53' from the intermediate transfer belt 12a, and this diffused reflection component is not incident on the light receiving element 35. Accordingly, as illustrated in FIG. 10B, in the toner detection unit 31 of the present embodiment, the output value 102 in the case where the light receiving element 35 receives light reflected from the surface of the intermediate transfer belt 12a is suppressed more than in the comparative example (FIG. 10D). This means that, in the output of the light receiving element 35, the amplitude component effective for the detection of toner becomes larger.

Next, a difference between the output value illustrated in FIG. 10B and the output value illustrated in FIG. 10D in a case where the test pattern 30 is formed on the irradiation region 54 of the LED 33 (the light-receivable region 56) is described. Here, when focusing on the output value of the light receiving element 35 in the case where reflected light from the toner image (solid image) of a density of 100% is received, the output value illustrated in FIG. 10B is larger than the output value (comparative example) illustrated in FIG. 10D. This is because while the toner detection unit 231 of the comparative example has a configuration in which the distance between the LED 33 and the light receiving element 35 is relatively long, the toner detection unit 31 of the present embodiment has a configuration in which the distance between the LED 33 and the light receiving element 35 is relatively short. That is, since for the toner detection unit 31 of the present embodiment, the optical path length (LD1+LD2) of light that the light receiving element 35 receives is shorter than for the toner detection unit 231 of the comparative example, the diffused reflection light can be received at a higher intensity.

In this way, the housing 37 mounted to the circuit board 36 is configured in the toner detection unit 31 of the present embodiment such that the light-receivable region 55 for the light receiving element 34 and the light-receivable region 56 for the light receiving element 35 are regions that do not overlap each other. This configuration enables a relatively large received light amount in the case where the light receiving element 35 receives diffused reflection light from the toner image, while relatively reducing the received light amount in the case where the light receiving element 35 receives diffused reflection light from the surface of the intermediate transfer belt 12a. In the toner detection unit 31 of the present embodiment, the light receiving element 35 which receives the diffused reflection light of the light that the LED 33 (light emitting element) emits is further arranged at a position that is closer to the LED 33 than the light receiving element 34 that receives the specular reflection light of the light that the LED 33 emits. This configuration further enables a relatively larger received light amount in the case where the light receiving element 35 receives diffused reflection light from a toner image. Note that the toner detection unit 31 is configured such that the common LED 33 (light emitting element) is able to sufficiently irradiate light (that is, so that both the light-receivable regions 55 and 56 are included in the irradiation region 54) towards both the light-receivable regions 55 and 56.

By virtue of the configuration of the toner detection unit 31 of the present embodiment, the output value 102 of the light receiving element 35 in a case where light reflected from the surface of the intermediate transfer belt 12a is received becomes smaller than the output value of the toner detection unit 231 of the comparative example. Also, the output value of the light receiving element 35 in the case where light reflected from a toner image of the maximum density (100%) is received becomes larger than the output value of the toner detection unit 231 of the comparative example. That is, by virtue of the configuration of the toner detection unit 31 of the present embodiment, it is possible to increase the difference (for example the difference 103) between the output value of the light receiving element 35 in cases of receiving light reflected from toner images of each density and the output value 102 (minimum value).

Accordingly, in the toner detection unit 31 of the present embodiment, it is possible to determine, at a higher precision than in the comparative example, the existence or absence of toner in the light-receivable region 56 and the toner density, based on the light reception result by the light receiving element 35 of diffused reflection light of the light emitted from the LED 33. That is, with respect to the capability of toner detection (determination of the existence or absence of toner and density) based on the light reception result of diffused reflection light of the light emitted from the LED 33, the toner detection unit 31 of the present embodiment has a superior capability than the toner detection unit 231 of the comparative example.

<Other Characteristics of Toner Detection Unit 31>

The toner detection unit 31 of the present embodiment, as illustrated in FIGS. 5A and 5B, is configured so that the light-receivable region 56 for the light receiving element 35 that receives diffused reflection light is wider than the light-receivable region 55 for the light receiving element 34 that receives the specular reflection light. As described above using FIGS. 10A to 10D, the specular reflection light of the light emitted from the LED 33 is strong light having a comparatively high directivity. In contrast to this, the diffused reflection light of the light emitted from the LED 33 is scattered in various directions and is weak light that has a low directivity. Accordingly, in the present embodiment, the light-receivable region 56 for receiving the diffused reflection light is made to be wider than the light-receivable region 55 for receiving the specular reflection light so that the received light amount of the diffused reflection light by the light receiving element 35 becomes greater. That is, as illustrated in FIGS. 5A and 5B, the size of the light-receivable region 56 is larger than that of the light-receivable region 55 in the direction in which the light receiving element 34 and the light receiving element 35 are arranged.

Also, in the toner detection unit 31 of the present embodiment, light emitted from the LED 33 (light emitting element) is emitted from the housing 37 through the light guiding path 60 which is arranged in the housing 37. The diffused reflection light of the light emitted from the LED 33 is incident on the light receiving element 35 through the light guiding path 62. That is, the toner detection unit 31 is configured so that an outlet from the housing 37 for light emitted from the LED 33, and an inlet into the housing 37 for diffused reflection light that the light receiving element 35 receives are common. That is, in the housing 37, a common opening for narrowing light emitted from the LED 33 and light to be incident on the light receiving elements 34 and 35 is formed. With this, it is possible to enable the distance between the LED 33 and the light receiving element 35 to be made shorter compared to a case where the outlet of light emitted from the LED 33 and the inlet of diffused reflection light differ. As a result, it is possible to shorten the optical path length (LD1+LD2) of light that the light receiving element 35 receives, and to also shorten the optical path length (LS1+LS2) of light that the light receiving element 34 receives. Accordingly, it is possible to increase the amount of light that each of the light receiving elements 34 and 35 receives and to make the output values from each light receiving element which indicate the light reception result be larger values.

Note that in the present embodiment, the two light receiving elements 34 and 35 are integrated to miniaturize the toner detection unit 31, but they may be arranged as independent circuit elements in proximity at positions similar to in the present embodiment. In such cases, it is also possible to realize a toner detection unit 31 capable of achieving advantages similar to the present embodiment.

As described above, the toner detection unit 31 of the present embodiment includes the LED 33 that irradiates light towards the intermediate transfer belt 12a, and the light receiving elements 34 and 35 that respectively receives the specular reflection light and the diffused reflection light of the light emitted from the LED 33. The LED 33 and the light receiving elements 34 and 35 are mounted in a line on the circuit board 36. A light guiding path that guides the light emitted from the LED 33 towards the intermediate transfer belt 12a and a light guiding path that guides specular reflection light and diffused reflection light respectively to the light receiving elements 34 and 35 are provided for the circuit board 36. Specifically, the housing 37 is configured to guide, to the light receiving element 34, the specular reflection light from the light-receivable region 55 within the irradiation region 54 of the LED 33 and to guide, to the light receiving element 35, the diffused reflection light from the light-receivable region 56 which is different to the light-receivable region 55 within the irradiation region 54. According to the present embodiment, it is possible to realize a superior (over the toner detection unit 231 of the comparative example) capability regarding a capability for toner detection based on the light reception result of the diffused reflection light while realizing miniaturization of the size, in the arrangement direction of the LED 33 and the light receiving elements 34 and 35, of the toner detection unit 31.

Second Embodiment

In the second through fifth embodiments, as examples of usage of the toner detection unit 31 explained in the first embodiment, examples in which color misregistration correction control using test patterns that are advantageous for detection by the toner detection unit 31 is performed are described.

Generally, in color misregistration, there is color misregistration due to static causes (static color misregistration) and color misregistration due to dynamic causes (dynamic color misregistration), for which the color misregistration amount fluctuates periodically. Static causes are an error in a write start position of an image or the like. Dynamic causes are velocity fluctuations of a conveyance belt (a print material conveyance belt, an intermediate transfer belt, or the like) due to unevenness of driving of a driving roller for the conveyance belt, unevenness of rotation of a photosensitive drum, or the like. If a test pattern formed on the intermediate transfer belt is detected by an optical sensor to measure a (static) color misregistration amount, an error will arise in that measurement result due to a dynamic color misregistration component of a degree dependent on the detection timing of the test pattern. (for example, see Japanese Patent Laid-Open No. 2002-14507.) Such a dynamic color misregistration component becomes larger the more the timings (phases of fluctuation for a dynamic color misregistration component) at which patch images of a reference color and a target color for color misregistration amount measurement are detected is displaced.

To reduce the foregoing measurement error, as recited in, for example, Japanese Patent Laid-Open No. 2002-14507, it is necessary to be able to cancel the dynamic color misregistration component by forming a plurality of patterns corresponding to a plurality of phases of the dynamic color misregistration component in a movement direction of the conveyer belt. However, if forming a plurality of patterns in the movement direction (the sub-scanning direction) of the conveyance belt, there is a problem in that the total length of the plurality of patterns in the sub-scanning direction becomes longer and the time required for the color misregistration correction control (calibration) also becomes longer.

In contrast to this, if the toner detection unit 31 illustrated in FIG. 4 and FIGS. 5A and 5B is used, as described above, it is possible to detect toner images simultaneously in two different regions (the light-receivable regions 55 and 56) on the intermediate transfer belt 12a. Accordingly, in the present embodiment, using this characteristic of the toner detection unit 31, a test pattern in which patch images of the reference color and the target color are arranged at the same position in the sub-scanning direction (that is, at approximately the same phase) is formed. This enables these patch images to be detected by the light receiving elements 34 and 35. If it is possible to detect the patch images of the reference color and the target color at a timing for which the phases of the fluctuation for the dynamic color misregistration component are of the same phase in this way, it becomes possible to measure a (static) color misregistration amount without experiencing the influence of a dynamic color misregistration component. In such a case, it is advantageous in that it is unnecessary to form a plurality of test patterns corresponding to a plurality of phases as described above in order to cancel the dynamic color misregistration component. Below, the present embodiment is described focusing on points of difference with the first embodiment.

<Example of a Test Pattern>

In the present embodiment, a case in which the reflectance of the intermediate transfer belt 12a in the light source wavelengths of the toner detection unit 31 (optical sensor) is higher than the toner image of any color for specular reflection light, and lower than the toner image of any color for diffused reflection light is described. In such a case, it is possible to detect both the specular reflection light and the diffused reflection light from the intermediate transfer belt 12a well by the toner detection unit 31.

Figure 11:
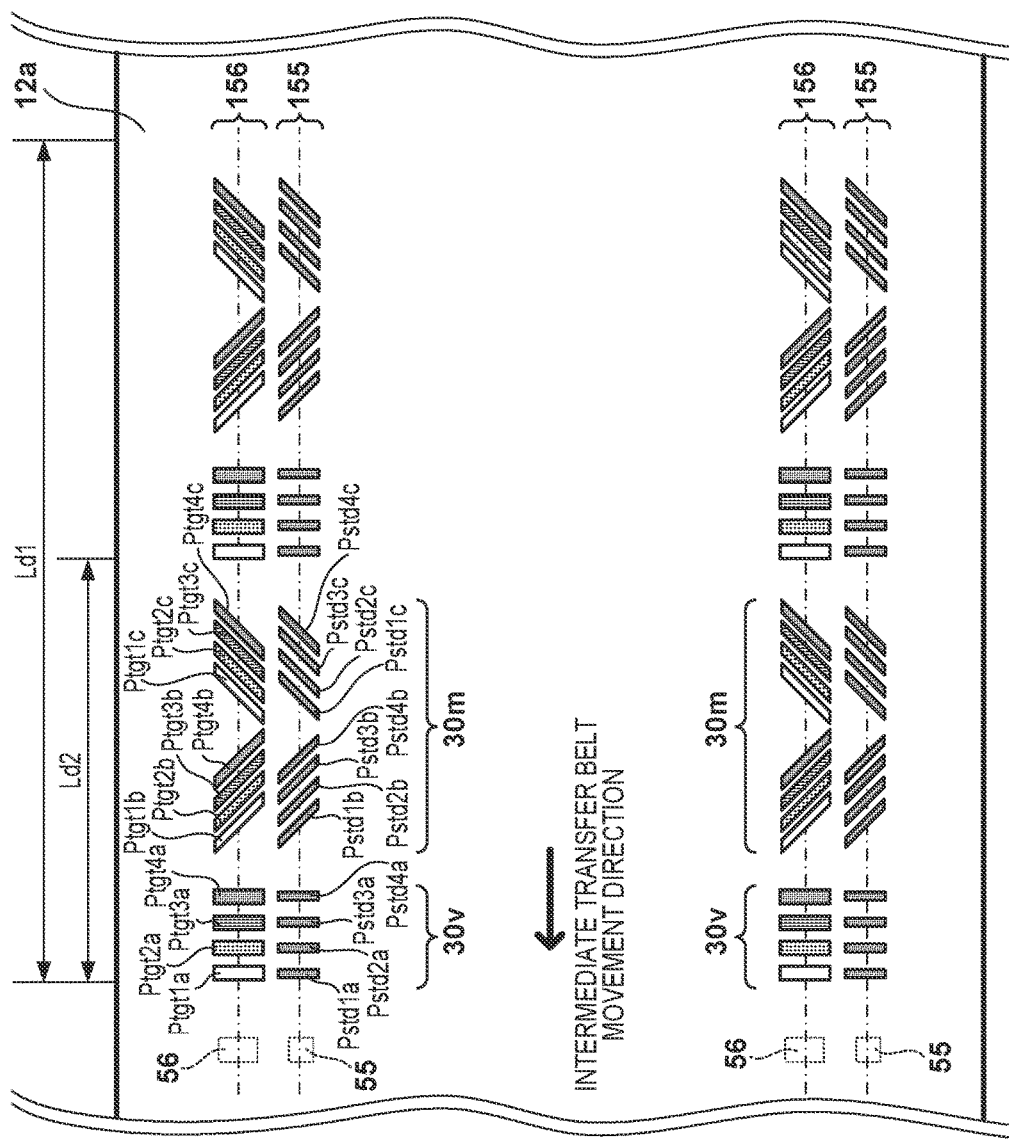
FIG. 11 illustrates an example of test patterns formed on an intermediate transfer belt (second through fifth embodiments).

FIG. 11 illustrates an example of the test pattern 30 in a distance Ld1 corresponding to one rotation period of the photosensitive drum 1. In FIG. 11, a region 155 on the intermediate transfer belt 12a corresponds to a region in which a toner image passes through the light-receivable region 55 for the light receiving element 34 during conveyance by the intermediate transfer belt 12a, in the case where the toner image is formed on that region. Also, a region 156 on the intermediate transfer belt 12a corresponds to a region in which a toner image passes through the light-receivable region 56 for the light receiving element 35 during conveyance by the intermediate transfer belt 12a, in the case where the toner image is formed on that region. Below, the region 155 will be referred to as "region for specular reflection light reception", and the region 156 as "region for diffused reflection light reception".

As illustrated in FIG. 11, independent test patterns (toner images) are formed in parallel in the region for specular reflection light reception 155 and the region for diffused reflection light reception 156, respectively. Also, a test pattern 30v for detecting a color misregistration amount in the sub-scanning direction and a test pattern 30m for detecting a color misregistration amount in the main scanning direction are arranged alternatingly along the movement direction of the surface of the intermediate transfer belt 12a (along the conveyance direction of the toner images). The test patterns 30v and 30m are respectively configured by a patch image group including a plurality of patch images which are a plurality of toner images (toner patches). In this way, the test pattern 30 of the present embodiment includes the test pattern 30v and the test pattern 30m. Note that the movement direction of the surface of the intermediate transfer belt 12a, and the direction orthogonal to the movement direction correspond to the sub-scanning direction and the main scanning direction in scanning of the photosensitive drum 1 by a laser beam.

The test pattern 30v includes reference color patch images Pstd1a, Pstd2a, Pstd3a, and Pstd4a used as references for color misregistration amount detection that are arranged in the sub-scanning direction on the region for specular reflection light reception 155 on the intermediate transfer belt 12a. The test pattern 30v further includes target color patch images Ptgt1a, Ptgt2a, Ptgt3a, and Ptgt4a that serve as targets of color misregistration amount detection where a reference color is used as a reference, and that are arranged in the sub-scanning direction on the region for diffused reflection light reception 156 on the intermediate transfer belt 12a. The target color patch images Ptgt1a, Ptgt2a, Ptgt3a, and Ptgt4a are arranged to be of approximately the same phase in the sub-scanning direction as reference color patch images Pstd1a, Pstd2a, Pstd3a, and Pstd4a, respectively. Note that the target color patch images Ptgt1a, Ptgt2a, Ptgt3a, and Ptgt4a are respectively formed using different color toner.

The test pattern 30m includes the reference color patch images Pstd1b, Pstd2b, Pstd3b, and Pstd4b, and the reference color patches Pstd1c, Pstd2c, Pstd3c, and Pstd4c which are arranged in the sub scanning direction of the region for specular reflection light reception 155 on the intermediate transfer belt 12a. The test pattern 30m further includes the target color patch images Ptgt1b, Ptgt2b, Ptgt3b, and Ptgt4b, and the target color patch images Ptgt1c, Ptgt2c, Ptgt3c, and Ptgt4c which are arranged in the sub-scanning direction of the region for diffused reflection light reception 156 on the intermediate transfer belt 12a. The target color patch images Ptgt1b, Ptgt2b, Ptgt3b, and Ptgt4b are arranged to be of approximately the same phase in the sub-scanning direction as reference color patch images Pstd1b, Pstd2b, Pstd3b, and Pstd4b, respectively. Also, the target color patch images Ptgt1c, Ptgt2c, Ptgt3c, and Ptgt4c are arranged to be of approximately the same phase in the sub scanning direction as reference color patch images Pstd1c, Pstd2c, Pstd3c, and Pstd4c, respectively. Note that, the target color patch images Ptgt1b, Ptgt2b, Ptgt3b, and Ptgt4b are formed using respectively different color toner, and the target color patch images Ptgt1c, Ptgt2c, Ptgt3c, and Ptgt4c are formed using respectively different color toner.

In the example of FIG. 11, the test pattern 30v is formed, in the sub-scanning direction, repeatedly in intervals of a distance Ld2 of an inverse phase corresponding to half a rotation period of the photosensitive drum 1. With this, by repeating the pattern, it is possible to cancel a detection error component of a color misregistration amount due to unevenness of rotation of the photosensitive drum 1. Note that a test pattern corresponding to ⅓ the rotation period, ¼ the rotation period or the like of the photosensitive drum 1 may additionally be formed depending on the region in which formation of a test pattern on the intermediate transfer belt 12a is possible. With this, it becomes possible to cancel a detection error component of a color misregistration amount due to unevenness of rotation of the photosensitive drum 1 at a higher precision.

<Color Misregistration Amount Detection in Sub-Scanning Direction>

Next, with reference to FIG. 12A, a method for detecting (measuring) the color misregistration amount of a target color with respect to a reference color in the sub scanning direction using the test pattern 30v illustrated in FIG. 11 is described. Here, detection of a color misregistration amount of a target color with respect to a reference color in a case where the reference color is assumed to be black (K) and the target color is assumed to be yellow (Y) is described as an example.

FIG. 12A magnifies the patch image Pstd1a of K which is the reference color, and the patch image Ptgt1a of Y which is the target color, as a portion of the test pattern 30v illustrated in FIG. 11. As described above, the patch image Pstd1a of the reference color (K) and the patch image Ptgt1a of the target color (Y) respectively have sizes that conform to the size of the light-receivable regions 55 and 56. As described in the first embodiment, because the light-receivable region 56 is wider than the light-receivable region 55, the patch image Ptgt1a of the target color (Y) is of a larger size in the main scanning direction and the sub-scanning direction than the patch image Pstd1a of the reference color (K).

The patch image Pstd1a formed on the region for specular reflection light reception 155 passes through the light-receivable region 55 for the light receiving element 34 included in the toner detection unit 31 while being conveyed in conjunction with movement of the surface of the intermediate transfer belt 12a. The control unit 41 (CPU) detects the leading end and the trailing end in the sub scanning direction of the patch image Pstd1a, based on the light reception result, by the light receiving element 34, of the specular reflection light from the intermediate transfer belt 12a and the patch image Pstd1a. The control unit 41 detects the detection timing Tstd1ap of the leading end of the patch image Pstd1a and the detection timing Tstd1as of the trailing end of the patch image Pstd1a, respectively as the leading end and trailing end positions of the patch image.

Meanwhile, the patch image Ptgt1a formed on the region for diffused reflection light reception 156 passes through the light-receivable region 56 for the light receiving element 35 included in the toner detection unit 31 while being conveyed in conjunction with movement of the surface of the intermediate transfer belt 12a. The control unit 41 detects the leading end and the trailing end in the sub-scanning direction of the patch image Ptgt1a, based on the light reception result, by the light receiving element 35, of the diffused reflection light from the intermediate transfer belt 12a and the patch image Ptgt1a. The control unit 41 detects the detection timing Ttgt1ap of the leading end of the patch image Ptgt1a and the detection timing Ttgt1as of the trailing end of the patch image Ptgt1a, respectively as the leading end and trailing end positions of the patch image.

The control unit 41 calculates, from the data obtained in this way, a center position Tstd1a between the leading end Tstd1ap and a trailing end Tstd1as of the patch image Pstd1a of the reference color (K) and a center position Ttgt1a between the leading end Ttgt1ap and the trailing end Ttgt1as of the patch image Ptgt1a of the target color (Y). Furthermore, the control unit 41 calculates a difference Dtgt1a between the center position Tstd1a of the patch image Pstd1a of the reference color (K) and the center position Ttgt1a for the patch image Ptgt1a of the target color (Y) (=Ttgt1a−Tstd1a), as the color misregistration amount of the target color (Y) with respect to the reference color (K) in the sub-scanning direction. The control unit 41 can perform the foregoing color misregistration correction control (for example, color misregistration correction in the sub-scanning direction by adjusting the write start timing) by using this calculation result of the color misregistration amount.

<Color Misregistration Amount Detection in Main Scanning Direction>

Next, with reference to FIG. 12B, a method for detecting (measuring) the color misregistration amount of a target color with respect to a reference color in the main scanning direction using the test pattern 30m illustrated in FIG. 11 is described. Here, similarly to FIG. 12A, detection of a color misregistration amount of a target color with respect to a reference color in a case where the reference color is assumed to be black (K) and the target color is assumed to be yellow (Y) is described as an example.

FIG. 12B magnifies the patch image Pstd1b of K which is the reference color, and the patch image Ptgt1b of Y which is the target color, as a portion of the test pattern 30m illustrated in FIG. 11. As illustrated in FIG. 12B, for each patch image, there is an angle of inclination 45° with respect to the movement direction (the sub scanning direction) of the surface of the intermediate transfer belt 12a in order to enable detection of the color misregistration amount in the main scanning direction. Also, as described above, the patch image Pstd1b and the patch image Ptgt1b are arranged so as to be in approximately the same phase in the sub-scanning direction.

The patch image Pstd1b formed on the region for specular reflection light reception 155 passes through the light-receivable region 55 for the light receiving element 34 while being conveyed in conjunction with movement of the surface of the intermediate transfer belt 12a. The control unit 41, based on the light reception result of the specular reflection light by the light receiving element 34, detects the leading end and the trailing end in the sub scanning direction of the patch image Pstd1b. The control unit 41 detects the detection timing Tstd1bp of the leading end of the patch image Pstd1b and the detection timing Tstd1bs of the trailing end, respectively as the leading end and trailing end positions of the patch image.

Meanwhile, the patch image Ptgt1b formed on the region for diffused reflection light reception 156 passes through the light-receivable region 56 of the light receiving element 35 while being conveyed in conjunction with movement of the surface of the intermediate transfer belt 12a. The control unit 41, based on the light reception result of the diffused reflection light by the light receiving element 35, detects the leading end and the trailing end in the sub scanning direction of the patch image Ptgt1b. The control unit 41 detects the detection timing Ttgt1bp of the leading end of the patch image Ptgt1b and the detection timing Ttgt1bs of the trailing end, respectively as the leading end and trailing end positions of the patch image.

The control unit 41 calculates, from the data obtained in this way, a center position Tstd1b between the leading end Tstd1bp and a trailing end Tstd1bs of the patch image Pstd1b of the reference color (K) and a center position Ttgt1b between the leading end Ttgt1bp and the trailing end Ttgt1bs of the patch image Ptgt1b of the target color (Y). Furthermore, the control unit 41 calculates a difference Dtgt1b between the center position Tstd1b of the patch image Pstd1b of the reference color (K) and the center position Ttgt1b for the patch image Ptgt1b of the target color (Y) (=Ttgt1b−Tstd1b). Here, the angle of inclination of each patch image included in the test pattern 30m is 45°. Accordingly, it is possible to handle the calculated Dtgt1b as a color misregistration amount in the main scanning direction of the target color (Y) with respect to the reference color (K) under a condition that there is no color misregistration in the sub-scanning direction. The control unit 41 can perform the foregoing color misregistration correction control (for example, color misregistration correction in the main scanning direction by adjusting the write start timing or the like) by using this color misregistration amount calculation result.

As described above, in the present embodiment, using the fact that the light-receivable regions 55 and 56 of the toner detection unit 31 do not overlap, the test pattern 30 in which patch images of the reference color and the target color are arranged at approximately the same phase in the sub-scanning direction are formed on the intermediate transfer belt 12a. Furthermore, the color misregistration amount is detected (measured) by using the light receiving elements 34 and 35 to detect the test pattern 30.

By using the toner detection unit 31 described in the first embodiment in this way, it is possible to detect the color misregistration amount using the patch images of the reference color and the target color formed at approximately the same phase in the sub-scanning direction. With this, it is possible to detect a color misregistration amount while removing a dynamic color misregistration component (other than dynamic color misregistration component due to an error in the distance between the photosensitive drums) of the intermediate transfer belt 12a. That is, because canceling processing for such as at ¼ the rotation period of the intermediate transfer belt 12a, for example, becomes unnecessary, there ceases to be a need to form a plurality of test patterns corresponding to a plurality of phases of a dynamic color misregistration component in order to cancel the dynamic color misregistration component. Accordingly, it is possible to improve the precision of detection of the color misregistration amount corresponding to a unit length of the test pattern, and possible to shorten the overall length of the test pattern 30 in the sub-scanning direction. With this, it is possible to reduce the toner consumption amount for forming the test pattern 30, and it is possible to shorten the time required for detection of the color misregistration amount and the time required for the color misregistration correction control.

Note that in the present embodiment, detection of the color misregistration amount in the sub-scanning direction and the main scanning direction is described assuming that the reference color is black (K) and the target color is yellow (Y), but it is possible to detect the color misregistration amount similarly for other color combinations. Also, the test patterns 30v and 30m (FIG. 11) used in the present embodiment are merely examples, and test patterns having different characteristics such as a pattern shape, a pattern interval, a color combination or the like may be employed. Additionally, the order of the patch images for the target color in the sub-scanning direction may be different to the order illustrated in FIG. 11. In the present embodiment, an example in which a reference color patch image is formed on the region for specular reflection light reception 155 on the light receiving element 34 side and a target color patch image is formed in the region for diffused reflection light reception 156 on the light receiving element 35 side is illustrated. However, a reference color patch image may be formed on the region for specular reflection light reception 155 on the light receiving element 34 side and a target color patch image may be formed in the region for diffused reflection light reception 156 on the light receiving element 35 side.

Third Embodiment

In the third embodiment, an example is described in which relative positional misalignment in the sub-scanning direction and the main scanning direction of the light receiving elements 34 and 35 mounted on the same circuit board 36 in the toner detection unit 31 described in the foregoing embodiment is corrected. Below, the present embodiment is described focusing on points of difference with the first and second embodiments.

In the second embodiment, by making the reference color and the target color different colors, a color misregistration amount between the reference color and the target color is detected. In contrast to this, it is possible to detect a relative positional misalignment amount of the light receiving elements 34 and 35 on the toner detection unit 31 (on the circuit board 36) when processing similar to the detection of the color misregistration amount in the second embodiment is performed where the reference color and the target color are made to be the same color. In the present embodiment, it is assumed that the reference color and the target color are the same color, black (K) as an example, and the relative positional misalignment amount of the light receiving element 35 with the position of the light receiving element 34 as a reference is detected.

<Positional Misalignment Amount Detection in Sub-Scanning Direction>

FIG. 13A magnifies the patch image Pstd4a which is the reference color, and the patch image Ptgt4a which is the target color and is the same color as the reference color, as a portion of the test pattern 30v illustrated in FIG. 11. As described in the second embodiment, the reference color patch image Pstd4a is formed on the region for specular reflection light reception 155 and the target color patch image Ptgt4a is formed on the region for diffused reflection light reception 156.

The control unit 41, based on the light reception result of the specular reflection light by the light receiving element 34, detects the leading end Tstd4ap and the trailing end Tstd4as in the sub scanning direction of the patch image Pstd4a of the reference color formed in the region for specular reflection light reception 155. Also, the control unit 41, based on the light reception result of the diffused reflection light by the light receiving element 35, detects the leading end Ttgt4ap and the trailing end Ttgt4as in the sub scanning direction of the patch image Ptgt4a of the target color formed in the region for diffused reflection light reception 156. The control unit 41 calculates, from data obtained in this way, the center position Tstd4a of the patch image Pstd4a of the reference color (K) and the center position Ttgt4a of the patch image Ptgt4a of the target color (K). Furthermore, the control unit 41 calculates the difference Dsns4a of these center positions (Dsns4a=Ttgt4a−Tstd4a) as the positional misregistration amount in the sub-scanning direction between the light receiving element 34 and the light receiving element 35.

The control unit 41 performs color misregistration correction control using the calculated positional misregistration amount Dsns4a as a correction value for the detected value Dtgt1a of the color misregistration amount in the second embodiment. That is, the control unit 41 performs the above described color misregistration correction control (for example, color misregistration correction of a sub-scanning direction by an adjustment of write start timing or the like) using a value (=Dtgt1a+Dsns4a) obtained by correcting the detected value Dtgt1a of the color misregistration amount by the positional misalignment amount Dsns4a. With this, it is possible to improve correction precision in the color misregistration correction control.

<Positional Misalignment Amount Detection in Main Scanning Direction>

FIG. 13B magnifies the patch image Pstd4b which is the reference color, and the patch image Ptgt4b which is the target color and is the same color as the reference color, as a portion of the test pattern 30m illustrated in FIG. 11. As described in the second embodiment, the reference color patch image Pstd4b is formed on the region for specular reflection light reception 155 and the target color patch image Ptgt4b is formed on the region for diffused reflection light reception 156. In order to enable detection of the positional misalignment amount in the main scanning direction of the light receiving elements 34 and 35, similarly to in the second embodiment, each patch image has an angle of inclination of 45° with respect to the movement direction (the sub-scanning direction) of the surface of the intermediate transfer belt 12a.

The control unit 41, based on the light reception result of the specular reflection light by the light receiving element 34, detects the leading end Tstd4bp and the trailing end Tstd4bs in the sub-scanning direction of the patch image Pstd4b of the reference color formed in the region for specular reflection light reception 155. Also, the control unit 41, based on the light reception result of the diffused reflection light by the light receiving element 35, detects the leading end Ttgt4bp and the trailing end Ttgt4bs in the sub-scanning direction of the patch image Ptgt4b of the target color formed in the region for diffused reflection light reception 156. The control unit 41 calculates, from data obtained in this way, the center position Tstd4b of the patch image Pstd4b of the reference color (K) and the center position Ttgt4*b* of the patch image Ptgt4*b* of the target color (K). Furthermore, the control unit 41 calculates the difference Dsns4*b* of these center positions (Dsns4*b*=Ttgt4*b*−Tstd4*b*) as the positional misalignment amount in the main scanning direction between the light receiving element 34 and the light receiving element 35.

The control unit 41 performs color misregistration correction control using the calculated positional misalignment amount Dsns4*b* as a correction value for the detected value Dtgt1*b* of the color misregistration amount in the second embodiment. That is, the control unit 41 performs the above described color misregistration correction control (for example, color misregistration correction of the main scanning direction by an adjustment of write start timing or the like) using a value (=Dtgt1*b*+Dsns4*b*) obtained by correcting the detected value Dtgt1*b* of the color misregistration amount by the positional misregistration amount Dsns4*b*. With this, it is possible to improve correction precision in the color misregistration correction control.

As described above, in the present embodiment, it is possible to detect the relative positional misalignment amount between the light receiving element 34 and the light receiving element 35 mounted on the same circuit board 36 by performing processing similar to the detection of the color misregistration amount in the second embodiment where the reference color and the target color are made to be the same color. Furthermore, by applying the detected positional misalignment amount to the color misregistration correction control in the second embodiment, it is possible to improve the precision of the color misregistration correction. Note that in the present embodiment, detection of the positional misalignment amount of the light receiving elements 34 and 35 is described assuming the reference color and the target color to be black (K), but it is possible to similarly detect a positional misalignment amount using other colors as well.

Fourth Embodiment

In the fourth embodiment, detection of the color misregistration amount in the case where the reflectance of the intermediate transfer belt 12*a* in the light source wavelength of the toner detection unit (optical sensor) differs from the reflectance in the second and third embodiments is described. Specifically, a case is described in which the reflectance of the intermediate transfer belt 12*a* is higher than that of toner images of any color for the specular reflection light, and lower than that of toner images of colors (Y, M, and C) other than black (K), but approximately equivalent to that of a toner image of K for diffused reflection light. In such a case, for toner images of colors (Y, M, and C) other than black (K), it is possible to detect at good precision by the toner detection unit 31 using either of the specular reflection light and the diffused reflection light. However, for a toner image of K, the received light amount by the light receiving element 35 becomes equivalent for the diffused reflection light from the region in which a toner image is formed on the intermediate transfer belt 12*a* and for a diffused reflection light from a region on which a toner image is not formed, and thus detection of the toner image becomes difficult.

Accordingly, the present embodiment is characterized in that, if a black (K) toner image is formed on the region for diffused reflection light reception 156 on the intermediate transfer belt 12*a*, a toner image for which the reflectance differs (is high) of a color other than K is formed as a base image of a K toner image. That is, by forming a K toner image overlappingly on a toner image of a color having a high reflectance other than K, detection precision of the boundaries of the K toner image can be enhanced. Note that the present embodiment is now described focusing on points of difference with the first through third embodiments.

Figure 14:
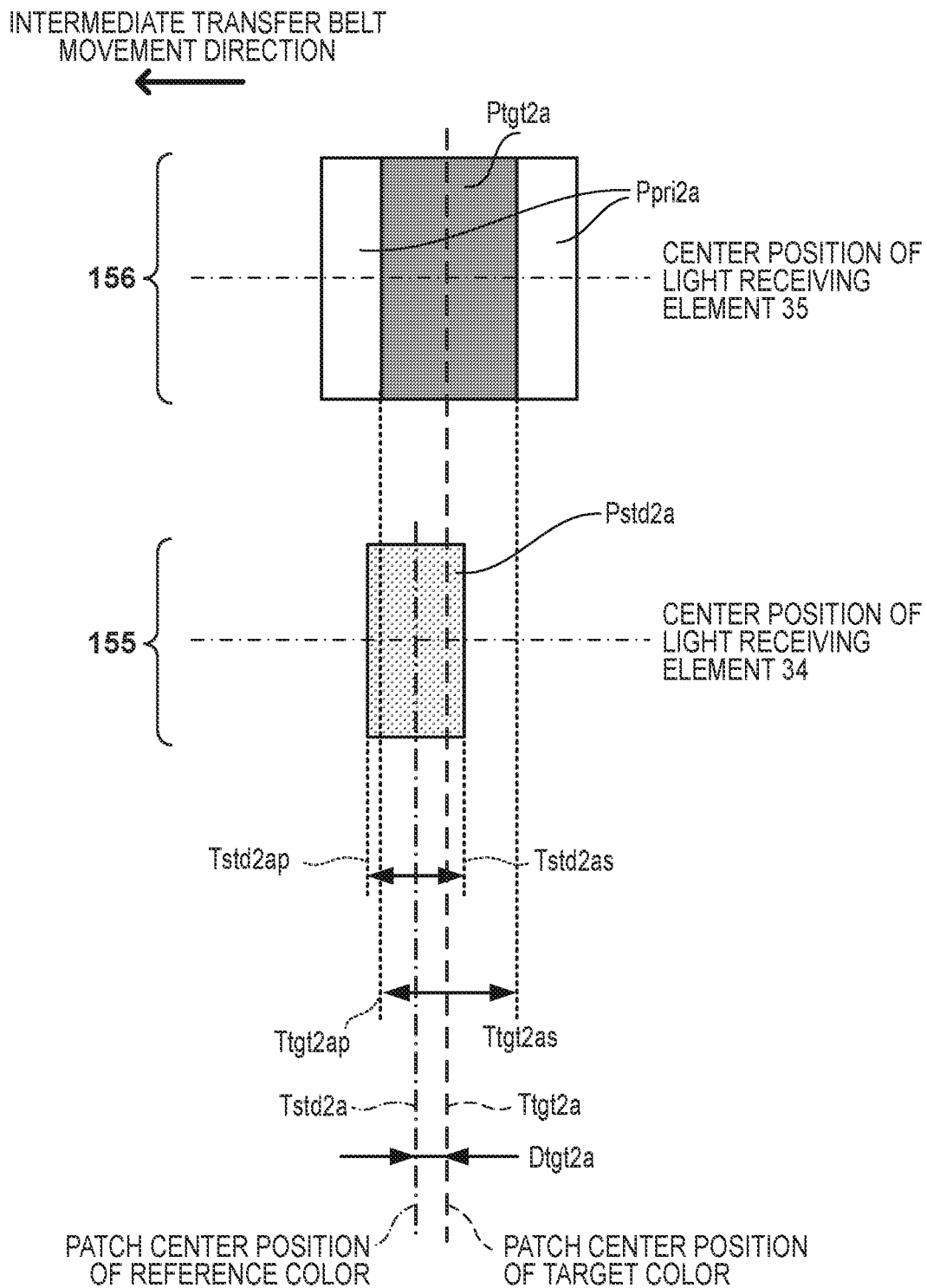
FIG. 14 illustrates an example of test patterns formed on an intermediate transfer belt (fourth embodiment).

In the present embodiment, detection of a color misregistration amount in the sub-scanning direction of a target color with respect to a reference color in a case where the reference color is assumed to be magenta (M) and the target color is assumed to be black (K) is described as an example. FIG. 14 magnifies the patch image Pstd2*a* which is the reference color (M), and the patch image Ptgt2*a* which is the target color (K), as a portion of the test pattern 30*v* illustrated in FIG. 11. The patch image Pstd2*a* of the reference color is formed on the region for specular reflection light reception 155 and the patch image Ptgt2*a* of the target color is formed on the region for diffused reflection light reception 156. In the present embodiment, a patch image Ppri2*a* of yellow (Y) whose size is larger than the patch image of the target color is formed on the region for diffused reflection light reception 156 as a base image of the patch image Ptgt2*a* of the target color (K). That is, the patch image Ptgt2*a* of K is formed overlappingly on the patch image Ppri2*a* of Y.

The control unit 41, similarly to the second and third embodiments, detects the leading end Tstd2*ap* and the trailing end Tstd2*as* in the sub-scanning direction of the patch image Pstd2*a* of the reference color (M) formed on the region for specular reflection light reception 155, based on a light reception result of specular reflection light by the light receiving element 34. Also, the control unit 41, based on the light reception result of the diffused reflection light by the light receiving element 35, detects the leading end Ttgt2*ap* and the trailing end Ttgt2*as* in the sub-scanning direction of the patch image Ptgt2*a* of the target color formed in the region for diffused reflection light reception 156. At that time, the control unit 41 detects the leading end and the trailing end of the patch image Ptgt2*a* from the boundaries between the patch image Ptgt2*a* of the target color and the patch image Ppri2*a* of Y formed as the base image.

The control unit 41 calculates, from data obtained in this way, the center position Tstd2*a* of the patch image Pstd2*a* of the reference color (M) and the center position Ttgt2*a* of the patch image Ptgt2*a* of the target color (K). Furthermore, the control unit 41 calculates a difference Dtgt2*a* (=Ttgt2*a*−Tstd2*a*) between the center position Tstd2*a* of the patch image Pstd2*a* of the reference color (M) and the center position Ttgt2*a* for the patch image Ptgt2*a* of the target color (K) as the color misregistration amount in the sub-scanning direction of the target color (K) with respect to the reference color (M). The control unit 41, by using this kind of color misregistration amount calculation result, can perform color misregistration correction control (for example, color misregistration correction in the sub-scanning direction by adjustment of the write start timing or the like) similarly to in the second and third embodiments.

As described above, in the present embodiment, for diffused reflection light, a base image is formed so that a difference in the reflectance between the base image and the patch image of the target color becomes larger than a difference in the reflectance between the surface of the intermediate transfer belt 12*a* and the patch image of the target color. By virtue of the present embodiment, it is possible to prevent the detection precision of the color misregistration amount from deteriorating in a case where a patch image of a color for which the ratio of the diffused reflection component included in the reflection light is low, such as black (K), is formed on the region for diffused reflection light reception 156 as the test pattern 30.

Note that in the present embodiment, detection of color misregistration amount in the sub-scanning direction is described assuming that the reference color is magenta (M), the target color is black (K) and the color of the patch image formed as the base image is yellow (Y), but it is possible to similarly detect a color misregistration amount for other combinations of colors. It is possible to realize detection of a color misregistration amount in the main scanning direction by similar processing to the second embodiment by forming a patch image that becomes a base image similarly to the test pattern 30v illustrated in FIG. 14. Also, the reflectance of the intermediate transfer belt 12a in the present embodiment is merely an example. For example, a similar advantage to that of the present embodiment can be expected when a toner image with a high reflectance is made to be the base image in a case where a toner image of a reflectance that is approximately equivalent to the reflectance of the intermediate transfer belt 12a is formed on the region for specular reflection light reception 155 or the region for diffused reflection light reception 156 on the intermediate transfer belt 12a.

Fifth Embodiment

In the fifth embodiment, a variation of the fourth embodiment is described. Generally, optical elements such as those used as the light receiving elements 34 and 35 of the toner detection unit 31 have the characteristic that the less the received light amount is the lower their response speed is. In the present embodiment, a method that realizes color misregistration amount detection and color misregistration correction control with better precision using the toner detection unit 31 taking into account such a difference of response speed of the optical elements depending on the received light amount is described. Note that the present embodiment is now described focusing on points of difference with the first through fourth embodiments.

Figure 15:
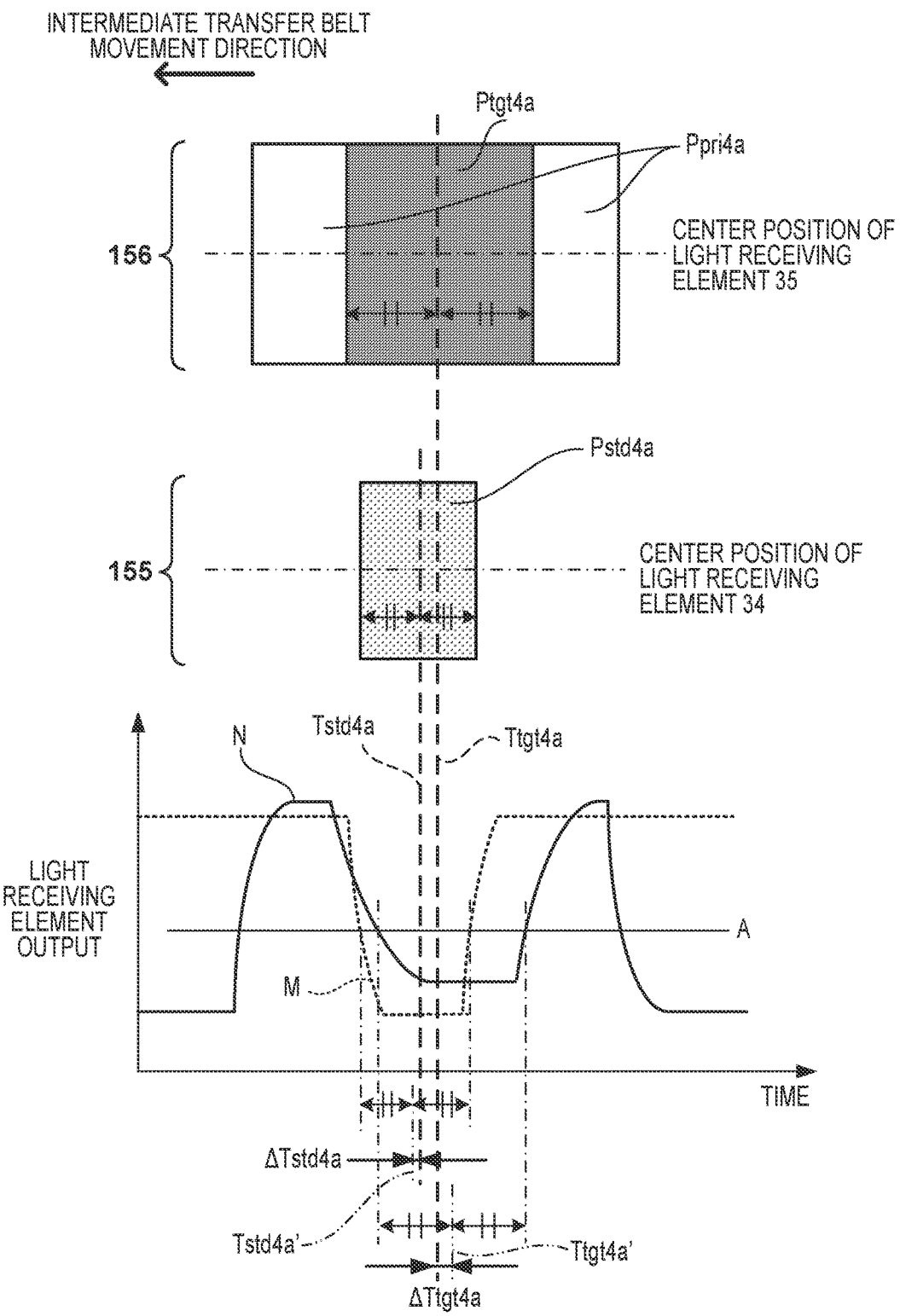
FIG. 15 illustrates an example of an output waveform of light receiving elements and test patterns formed on an intermediate transfer belt (fifth embodiment).

FIG. 15 illustrates a state in which, similarly to in FIG. 14, a patch image Pstd4a of a reference color (M) is formed on the region for specular reflection light reception 155, and a patch image Ppri4a of Y is formed in the region for diffused reflection light reception 156 as an under layer, and a patch image Ptgt4a of the target color (K) is formed overlappingly thereupon. FIG. 15 also illustrates a change in output of the light receiving elements 34 and 35 in the case where the light receiving elements 34 and 35 are used to detect the patch images formed on the region for specular reflection light reception 155 and the region for diffused reflection light reception 156.

In FIG. 15, the waveform M is an output waveform of the light receiving element 34, and the waveform N is an output waveform of the light receiving element 35. The output waveforms M and N, as illustrated in FIG. 15, are waveforms of shapes that are blunted in accordance with the received light amounts of the light receiving elements 34 and 35. The control unit 41 calculates, based on the output waveforms M and N which have such shapes and are outputted from the light receiving elements 34 and 35, center positions between two points at which the output waveforms M and N intersect a threshold voltage A, as center positions in the sub-scanning direction of the patch images. Accordingly, an error ΔTstd4a arises between the center position Tstd4a in the sub-scanning direction of the patch image Pstd4a formed in the region for specular reflection light reception 155 and the center position Tstd4a' calculated based on the output waveform M of the light receiving element 34. Similarly, an error ΔTtgt4a arises between the center position Ttgt4a in the sub-scanning direction of the patch image Ptgt4a formed in the region for diffused reflection light reception 156 and the center position Ttgt4a' calculated based on the output waveform N of the light receiving element 35.

As illustrated in FIG. 15, the degree of bluntness of the output waveforms of the light receiving elements 34 and 35 becomes larger as the received light amounts of the light receiving elements 34 and 35 are smaller, and as a result, the foregoing error becomes larger. In particular, the diffused reflection light that the light receiving element 35 receives is scattered in various directions and is weak light that has a low directivity. Accordingly, there is a tendency for a larger error to arise in a light reception result for diffused reflection light by the light receiving element 35 than in a light reception result for specular reflection light by the light receiving element 34.

In the present embodiment, color misregistration amounts in the sub-scanning direction for each color are detected so that the foregoing error is reduced. Specifically, the foregoing error is calculated by obtaining in advance output waveforms of the light receiving elements 34 and 35 as illustrated in FIG. 15 for each color, separately from the calibration in the image forming apparatus 100. Additionally, the calculated error is stored in advance as a correction value in a storage device such as a non-volatile memory (not shown) that the image forming apparatus 100 includes. That is, a correction value for correcting an error that arises in a detected value for a color misregistration amount due to the change in the response speed in accordance with the received light amount of the light receiving elements 34 and 35 is stored in the storage device. The control unit 41 uses this correction value to correct (offsets) color misregistration amounts obtained by the method described in the second through fourth embodiments. With this, it is possible to reduce a detection error of a color misregistration amount that arises due to the response speed of the light receiving elements 34 and 35.

Note that, in the present embodiment, detection of a color misregistration amount in the sub-scanning direction is described, but it is possible to implement similarly for detection of a color misregistration amount in the main scanning direction. Also, in the present embodiment, detection of a color misregistration amount in the sub-scanning direction is described assuming that the reference color is magenta (M), the target color is black (K) and the color of the patch image formed as the under layer is yellow (Y), but it is possible to similarly detect a color misregistration amount for other combinations of colors.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application is a continuation of U.S. patent application Ser. No. 15/297,381, filed Oct. 19, 2016, which claims the benefit of Japanese Patent Application No. 2015-218797, filed Nov. 6, 2015, both of which are hereby incorporated by reference herein in their entirety.

What is claimed is:
1. An optical sensor, comprising:
a light emitting element that irradiates irradiating light toward an irradiated member;

a first light receiving element for receiving diffused reflection light into which the irradiating light is diffusely reflected by the irradiated member;

a second light receiving element for receiving specular reflection light into which the irradiating light is specularly reflected by the irradiated member; and a housing for forming a first opening and a second opening, wherein the first opening is a common opening through which the irradiating light passes and through which the diffused reflection light to be received by the first light receiving element passes, and the second opening is an opening through which the specular reflection light to be received by the second light receiving element passes.

2. The optical sensor according to claim 1, wherein the housing forms, in a region between the first opening and the first light receiving element, a third opening through which the diffused reflection light that has passed through the first opening passes prior to being received by the first light receiving element.

3. The optical sensor according to claim 1, wherein the housing covers the light emitting element, the first light receiving element, and the second light receiving element.

4. The optical sensor according to claim 1, wherein a portion of a first light path through which the irradiating light passes and a portion of a second light path through which the diffused reflection light to be received by the first light receiving element passes overlap in a region up to where the irradiating light passes through the first opening.

5. The optical sensor according to claim 1, wherein the first light receiving element receives the diffused reflection light diffusely reflected by a first region within an irradiation region of the irradiated member onto which the irradiating light is irradiated, and the second light receiving element receives the specular reflection light specularly reflected by a second region within the irradiation region, at least a portion of which is different in a main scanning direction from the first region.

6. The optical sensor according to claim 5, wherein in a direction in which the first light receiving element and the second light receiving element are arranged, a region onto which the irradiating light is irradiated is larger for the first region than for the second region.

7. The optical sensor according to claim 5, wherein the first region and the second region are portions of the irradiation region, and do not overlap each other.

8. The optical sensor according to claim 1, wherein a distance between the first light receiving element and the light emitting element is shorter than a distance between the second light receiving element and the light emitting element.

9. The optical sensor according to claim 1, wherein the first light receiving element and the second light receiving element are arranged beside each other on a circuit board.

10. The optical sensor according to claim 1, wherein the housing has a light shielding wall for shielding light so that light other than the diffused reflection light is not received by the first light receiving element.

11. The optical sensor according to claim 10, wherein the light shielding wall is arranged above, in a vertical direction in relation to a mounting surface of a circuit board on which the first light receiving element and the second light receiving element are mounted, a position of the first light receiving element on the mounting surface.

12. The optical sensor according to claim 1, wherein the housing has a light shielding wall, arranged between the light emitting element and the first light receiving element, for shielding light so that light emitted from the light emitting element is not directly received by the first light receiving element and the second light receiving element.

13. The optical sensor according to claim 1, wherein the first light receiving element and the second light receiving element are mounted on a circuit board as a single integrated circuit.

14. An image forming apparatus, comprising:
an image carrier that is rotated;
the optical sensor according to claim 1, wherein the optical sensor is arranged at a position facing a surface of the image carrier and irradiates light toward the image carrier from the light emitting element; and
a control unit configured to, based on a signal outputted from the first light receiving element or the second light receiving element when an image formed on the image carrier passes through a first region or a second region within an irradiation region, detect a position or a density of the image, and execute a color misregistration correction control based on the detected position of the image or execute an image density control based on the detected density of the image.

15. An image forming apparatus, comprising:
an image carrier that is rotated;
the optical sensor according to claim 1, wherein the optical sensor is arranged at a position facing a surface of the image carrier such that a first region and a second region are arranged in a direction orthogonal to a movement direction of the surface of the image carrier, and emits light toward the image carrier from the light emitting element;
an image formation unit configured to form, on the surface of the image carrier, a first patch image that passes through the first region and a second patch image that is different in color from the first patch image and that passes through the second region, so as to be located at the same position in the movement direction; and
a control unit configured to detect a color misregistration amount based on a signal outputted from the first light receiving element when the first patch image passes through the first region and a signal outputted from the second light receiving element when the second patch image passes through the second region, and perform a color misregistration correction control based on the detected color misregistration amount.

16. The image forming apparatus according to claim 15, wherein
a length of the first patch image is longer in the direction orthogonal to the movement direction than a length of the second patch image.

17. The image forming apparatus according to claim 15, wherein
the control unit detects the color misregistration amount by detecting a position of the first patch image based on a signal outputted from the first light receiving element when the first patch image passes through the first region, and detecting a position of the second patch image based on a signal outputted from the second light receiving element when the second patch image passes through the second region.

18. The image forming apparatus according to claim 15, wherein the image formation unit further forms, on the surface of the image carrier, a third patch image that passes through the first region, and a fourth patch image of a color that is the same as that of the third patch image and that passes through the second region, so as to be located at the same position in the movement direction, the control unit further detects, as a positional misregistration amount between the first light receiving element and the second light receiving element, a difference between a position of the third patch image and a position of the fourth patch image, based on signals respectively outputted from the first light receiving element and the second light receiving element when the third patch image and the fourth patch image pass through the first region and the second region, respectively, and the control unit performs the color misregistration correction control based on the detected color misregistration amount and the positional misregistration amount.

19. The image forming apparatus according to claim 15, wherein when forming the first patch image, the image formation unit forms, as an under layer of the first patch image, a base image for which a reflectance is different from that of the first patch image and whose size is larger than that of the first patch image, and for the diffused reflection light, a difference of a reflectance between the base image and the first patch image is greater than the difference of the reflectance between the surface of the image carrier and the first patch image.

20. The image forming apparatus according to claim 15, further comprising a storage unit configured to store a correction value for correcting an error that arises in a detected value of the color misregistration amount due to a change in a response speed in accordance with received light amounts of the first light receiving element and the second light receiving element, wherein the control unit corrects the detected value of the color misregistration amount by the correction value stored in the storage unit.

21. An image forming apparatus, comprising:

an optical sensor; and an image formation unit, wherein the optical sensor comprises a light emitting element that irradiates irradiating light toward an irradiated member, a first light receiving element for receiving diffused reflection light into which the irradiating light is diffusely reflected in an irradiation region of the irradiated member, and a second light receiving element for receiving specular reflection light into which the irradiating light is specularly reflected in the irradiation region of the irradiated member, wherein the first light receiving element receives the diffused reflection light diffusely reflected in a first region within the irradiation region, and the second light receiving element receives the specular reflection light specularly reflected in a second region within the irradiation region, at least a part of which does not include the first region in a main scanning direction, and wherein the image formation unit forms, on a surface of the irradiated member, a first patch image that passes through the first region and a second patch image that passes through the second region.

* * * * *